United States Patent
Varner et al.

(10) Patent No.: US 11,344,559 B2
(45) Date of Patent: May 31, 2022

(54) PI3KGAMMA INHIBITORS

(71) Applicant: The Regents of the University of California, Oakland, CA (US)

(72) Inventors: Judith Varner, La Jolla, CA (US); Rommie Amaro, La Jolla, CA (US); Megan Kaneda, La Jolla, CA (US); Robert Malmstrom, La Jolla, CA (US); Victoria Feher, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/911,894

(22) Filed: Jun. 25, 2020

(65) Prior Publication Data

US 2020/0405730 A1    Dec. 31, 2020

Related U.S. Application Data

(60) Provisional application No. 62/867,020, filed on Jun. 26, 2019.

(51) Int. Cl.
| | | |
|---|---|---|
| *A61K 31/551* | (2006.01) | |
| *A61K 31/453* | (2006.01) | |
| *A61K 31/438* | (2006.01) | |
| *A61K 31/4196* | (2006.01) | |
| *A61K 31/444* | (2006.01) | |

(52) U.S. Cl.
CPC ........ *A61K 31/551* (2013.01); *A61K 31/4196* (2013.01); *A61K 31/438* (2013.01); *A61K 31/444* (2013.01); *A61K 31/453* (2013.01)

(58) Field of Classification Search
CPC .................................................. A61K 31/551
USPC ....................................................... 514/221
See application file for complete search history.

(56) References Cited

U.S. PATENT DOCUMENTS

| 4,639,454 A | 1/1987 | Hesson |
| 2010/0087466 A1 | 4/2010 | Sturgess et al. |

FOREIGN PATENT DOCUMENTS

| WO | WO-2004/028530 A1 | 4/2004 |

OTHER PUBLICATIONS

Garmy-Susini, et al., "PI3Kgamma activates integrin alpha4beta1 to establish a metastatic niche in lymph nodes," PNAS, May 28, 2013, vol. 110, No. 22, pp. 9042-9047.
Gunderson, et al., "Bruton Tyrosine Kinase-Dependent Immune Cell Cross-talk Drives Pancreas Cancer," Cancer Discovery, Mar. 2016, pp. 270-285.
Kaneda, et al., "Macrophage PI3Kgamma Drives Pancreatic Ductal Adenocarcinoma Progression," Cancer Discover, Aug. 2016, pp. 870-885.
Kaneda, et al., "PI3Kgamma is a molecular switch that controls immune suppression," Nature, Nov. 17, 2016, vol. 539, pp. 437-442.
Okkenhaug, et al., "Targeting PI3K in Cancer: Impact on Tumor Cells, Their Protective Stroma, Angiogenesis, and Immunotherapy," Cancer Discovery, Oct. 16, pp. 1090-1105.
Schmid, et al., "Combined Blockade of Integrin-alpha4beta1 Plus Cytokines SDF-1 alpha or IL-1 beta Potently Inhibits Tumor Inflammation and Growth," Cancer Research, Sep. 23, 2011, pp. 6965-6975.
Schmid, et al., "PI3-kinase gamma Promotes Rap1a-Mediated Activation of Myeloid Cell Integrin alpha4beta1, Leading to Tumor Inflammation and Growth," Plos One, Apr. 2013, vol. 8, Issue 4, e60226, 12 pages.
Schmid, et al., "Receptor tyrosine kinases and TLR/IL1Rs unexpectedly activate myeloid cell PI3Kgamma, a single convergent point promoting tumor inflammation and progression," Cancer Cell, Jun. 14, 2011, 19(6), pp. 715-727.
Stark, et al., "PI3K inhibitors in inflammation, autoimmunity and cancer," Curr. Opin. Pharmacol., Aug. 2015, vol. 23, pp. 82-91.
International Search Report and Written Opinion dated Nov. 19, 2020, from application No. PCT/US2020/039563.
PubChem-CID-130157556, Create Date: Oct. 7, 2017 (Oct. 7, 2017), p. 2.

*Primary Examiner* — Taofiq A Solola
(74) *Attorney, Agent, or Firm* — Foley & Lardner LLP

(57) ABSTRACT

The present disclosure relates to PI3Kγ inhibitors and methods of their use.

3 Claims, No Drawings

PI3KGAMMA INHIBITORS

CROSS-REFERENCE TO RELATED APPLICATIONS

This application claims the benefit of U.S. Provisional Patent Application No. 62/867,020, filed Jun. 26, 2019, which is incorporated by reference herein in its entirety.

STATEMENT OF GOVERNMENT SUPPORT

This invention was made with government support under CA167426 awarded by the National Institutes of Health (NIH). The government has certain rights in the invention.

BACKGROUND

The present technology relates generally to the field of phosphoinositide 3-kinase gamma (PI3Kgamma, PI3Kγ) inhibitors.

SUMMARY

Provided herein in one aspect are methods to inhibit the growth of a cancer cell or treat cancer or inflammatory disease in a subject in need thereof, the methods comprising, or alternatively consisting essentially of, or yet further consisting of, administering to the cell or the subject a compound of Formula I, Formula II, Formula III, Formula IV, or Formula V, or a stereoisomer, tautomer, or pharmaceutically acceptable salt thereof:

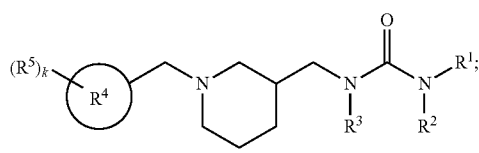

(Formula I)

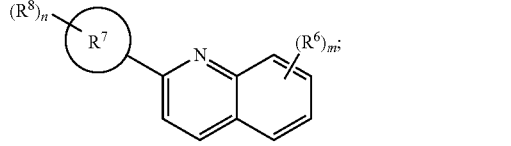

(Formula II)

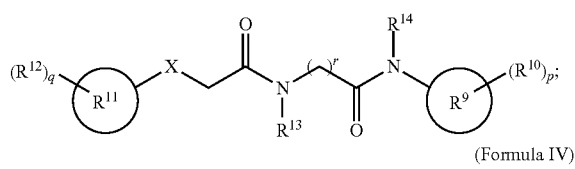

(Formula III)

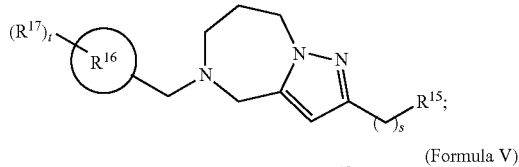

(Formula IV)

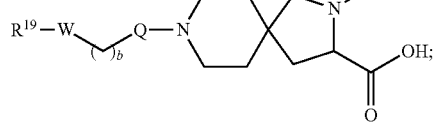

(Formula V)

wherein
$R^1$ is H or substituted or unsubstituted alkyl; $R^2$ is H or substituted or unsubstituted alkyl;
$R^3$ is H or substituted or unsubstituted alkyl; $R^4$ is aryl or heteroaryl;
each $R^5$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring; or two adjacent $R^5$, together with the atoms to which they are attached, form a substituted or unsubstituted cycloalkyl ring, a substituted or unsubstituted heterocyclyl ring, a substituted or unsubstituted aryl ring, or a substituted or unsubstituted heteroaryl ring;
each $R^6$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring;
$R^7$ is aryl or heteroaryl;
each $R^8$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring;
$R^9$ is aryl or heteroaryl;
each $R^{10}$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring;
$R^{11}$ is aryl or heteroaryl;
each $R^{12}$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring;
$R^{13}$ is H or substituted or unsubstituted alkyl; $R^{14}$ is H or substituted or unsubstituted alkyl;
$R^{15}$ is H, substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, or a substituted or unsubstituted heteroaryl ring;

R$^{16}$ is aryl or heteroaryl;

each R$^{17}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

R$^{18}$ is H, substituted or unsubstituted alkyl, —C(O)R$^m$, —C(O)OR$^m$, —C(O)NR$^m$R$^n$, —S(O)$_j$R$^m$, —S(O)$_j$NR$^m$R$^n$, a substituted or unsubstituted cycloalkyl ring, a substituted or unsubstituted heterocyclyl ring, a substituted or unsubstituted aryl ring, or a substituted or unsubstituted heteroaryl ring;

R$^{19}$ is H, substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, or a substituted or unsubstituted heteroaryl ring;

Q is —SO$_2$— or —C(O)—;

W is S, substituted or unsubstituted alkyl, a substituted or unsubstituted aryl ring, or a substituted or unsubstituted heteroaryl ring;

X is O or S;

each R$^m$, R$^n$, and R$^p$ is independently selected from the group consisting of H, substituted or unsubstituted alkyl, a substituted or unsubstituted cycloalkyl ring, a substituted or unsubstituted heterocyclyl ring, a substituted or unsubstituted aryl ring, and a substituted or unsubstituted heteroaryl ring b is 0 or 1; j is 1 or 2; k is 0, 1, 2, 3, 4 or 5; m is 0, 1, 2, 3, or 4; n is 0, 1, 2, 3, 4, or 5; p is 0, 1, 2, 3, 4, or 5; q is 0, 1, 2, 3, 4, or 5; r is 1, 2, 3, 4, or 5; s is 1, 2, 3, 4, or 5; and t is 1, 2, 3, 4, or 5. In one aspect, an effective amount is provided to the cell or subject, e.g., a therapeutically effective amount is provided to the cell or administered to subject.

Provided herein in another aspect are methods to stimulate M1 macrophage polarization, the methods comprising, or consisting essentially of, or yet further consisting of, contacting a macrophage with a compound of Formula I, Formula II, Formula III, Formula IV, or Formula V, or a stereoisomer, tautomer, or pharmaceutically acceptable salt thereof:

(Formula I)

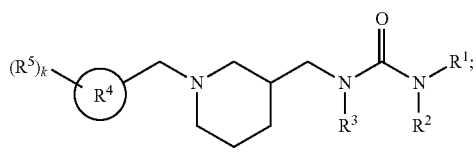

(Formula II)

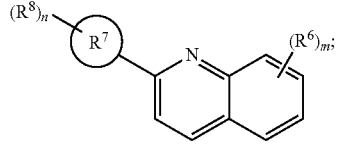

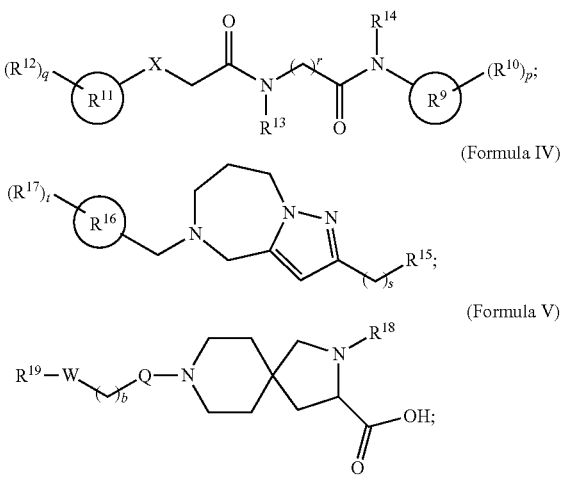

wherein

R$^1$ is H or substituted or unsubstituted alkyl; R$^2$ is H or substituted or unsubstituted alkyl;

R$^3$ is H or substituted or unsubstituted alkyl; R$^4$ is aryl or heteroaryl;

each R$^5$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring; or two adjacent R$^5$, together with the atoms to which they are attached, form a substituted or unsubstituted cycloalkyl ring, a substituted or unsubstituted heterocyclyl ring, a substituted or unsubstituted aryl ring, or a substituted or unsubstituted heteroaryl ring;

each R$^6$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

R$^7$ is aryl or heteroaryl;

each R$^8$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

R$^9$ is aryl or heteroaryl;

each R$^{10}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{11}$ is aryl or heteroaryl;

each $R^{12}$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring;

$R^{13}$ is H or substituted or unsubstituted alkyl; $R^{14}$ is H or substituted or unsubstituted alkyl;

$R^{15}$ is H, substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, or a substituted or unsubstituted heteroaryl ring;

$R^{16}$ is aryl or heteroaryl;

each $R^{17}$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring;

$R^{18}$ is H, substituted or unsubstituted alkyl, —$C(O)R'''$, —$C(O)OR'''$, —$C(O)NR'''R''$, —$S(O)_jR'''$, —$S(O)_jNR'''R''$, a substituted or unsubstituted cycloalkyl ring, a substituted or unsubstituted heterocyclyl ring, a substituted or unsubstituted aryl ring, or a substituted or unsubstituted heteroaryl ring;

$R^{19}$ is H, substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, or a substituted or unsubstituted heteroaryl ring;

Q is —$SO_2$— or —$C(O)$—;

W is S, substituted or unsubstituted alkyl, a substituted or unsubstituted aryl ring, or a substituted or unsubstituted heteroaryl ring;

X is O or S;

each $R'''$, $R''$, and $R^p$ is independently selected from the group consisting of H, substituted or unsubstituted alkyl, a substituted or unsubstituted cycloalkyl ring, a substituted or unsubstituted heterocyclyl ring, a substituted or unsubstituted aryl ring, and a substituted or unsubstituted heteroaryl ring b is 0 or 1; j is 1 or 2; k is 0, 1, 2, 3, 4 or 5; m is 0, 1, 2, 3, or 4; n is 0, 1, 2, 3, 4, or 5; p is 0, 1, 2, 3, 4, or 5; q is 0, 1, 2, 3, 4, or 5; r is 1, 2, 3, 4, or 5; s is 1, 2, 3, 4, or 5; and t is 1, 2, 3, 4, or 5.

In some embodiments, the contacting of the macrophage is performed in an in vitro assay. In some embodiments, the contacting of the macrophage is performed in an in vivo assay. In one aspect, a therapeutically effective amount is contacted.

Provided herein in another aspect are methods to inhibit M2 macrophage polarization, the methods comprising, or alternatively consisting essentially of, or yet further consisting of, contacting a macrophage with a compound of Formula I, Formula II, Formula III, Formula IV, or Formula V, or a stereoisomer, tautomer, or pharmaceutically acceptable salt thereof:

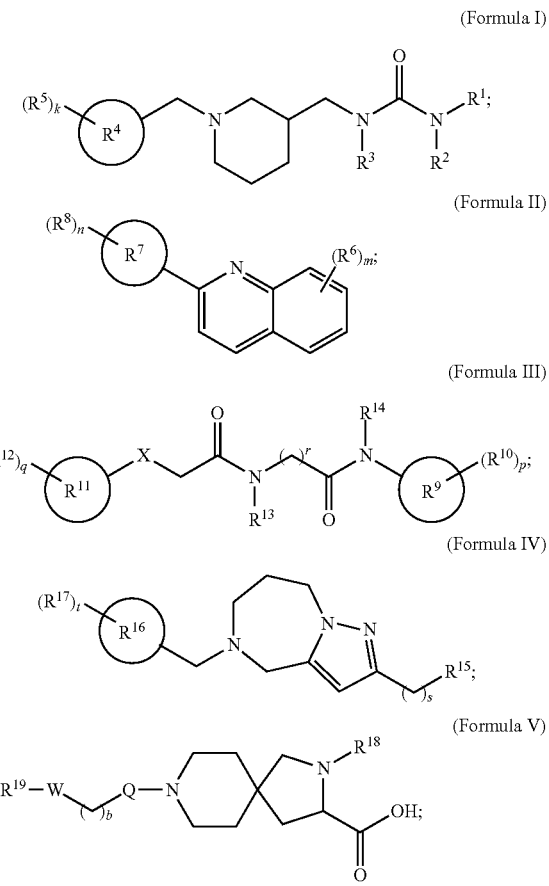

wherein $R^1$ is H or substituted or unsubstituted alkyl; $R^2$ is H or substituted or unsubstituted alkyl;

$R^3$ is H or substituted or unsubstituted alkyl; $R^4$ is aryl or heteroaryl;

each $R^5$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —$NR''C(O)R'''$, —$NR''C(O)OR'''$, —$NR''C(O)NR'''R^p$, —$NR''S(O)_jR'''$, —$NR''S(O)_jNR'''R^p$, a substituted or unsubstituted cycloalkyl ring, a substituted or unsubstituted heterocyclyl ring, a substituted or unsubstituted aryl ring, and a substituted or unsubstituted heteroaryl ring; or two adjacent $R^5$, together with the atoms to which they are attached, form a substituted or unsubstituted cycloalkyl ring, a substituted or unsubstituted heterocyclyl ring, a substituted or unsubstituted aryl ring, or a substituted or unsubstituted heteroaryl ring;

each $R^6$ is independently selected from the group consisting of substituted or unsubstituted alkyl, halide, —CN, —$NO_2$, —$SR'''$, —$OR'''$, —$NR'''R''$, —$C(O)R'''$, —$C(O)OR'''$, —$C(O)NR'''R''$, —$S(O)_jR'''$, —$S(O)_jNR'''R''$, —NR″C(O)R‴, —NR″C(O)OR‴, —NR″C(O)NR‴R^p, —NR″S(O)_jR‴, —NR″S(O)_jNR‴R^p, a substituted or unsubstituted cycloalkyl ring, a substituted or unsubstituted heterocyclyl ring, a substituted or unsubstituted aryl ring, and a substituted or unsubstituted heteroaryl ring;

$R^7$ is aryl or heteroaryl;

each $R^8$ is independently selected from the group consisting of substituted or unsubstituted alkyl, halide, —CN, —NO_2, —SR‴, —OR‴, —NR‴R″, —C(O)R‴, —C(O)OR‴, —C(O)NR‴R″, —S(O)_jR‴, —S(O)_jNR‴R″, —NR″C(O)R‴, —NR″C(O)OR‴, —NR″C(O)NR‴R^p, —NR″S(O)_jR‴, —NR″S(O)_jNR‴R^p, a substituted or unsubstituted cycloalkyl ring, a substituted or unsubstituted heterocyclyl ring, a substituted or unsubstituted aryl ring, and a substituted or unsubstituted heteroaryl ring;

$R^9$ is aryl or heteroaryl;

each $R^{10}$ is independently selected from the group consisting of substituted or unsubstituted alkyl, halide, —CN, —NO_2, —SR‴, —OR‴, —NR‴R″, —C(O)R‴, —C(O)OR‴, —C(O)NR‴R″, —S(O)_jR‴, —S(O)_jNR‴R″, —NR″C(O)R‴, —NR″C(O)OR‴, —NR″C(O)NR‴R^p, —NR″S(O)_jR‴, —NR″S(O)_jNR‴R^p, a substituted or unsubstituted cycloalkyl ring, a substituted or unsubstituted heterocyclyl ring, a substituted or unsubstituted aryl ring, and a substituted or unsubstituted heteroaryl ring;

$R^{11}$ is aryl or heteroaryl;

each $R^{12}$ is independently selected from the group consisting of substituted or unsubstituted alkyl, halide, —CN, —NO_2, —SR‴, —OR‴, —NR‴R″, —C(O)R‴, —C(O)OR‴, —C(O)NR‴R″, —S(O)_jR‴, —S(O)_jNR‴R″, —NR″C(O)R‴, —NR″C(O)OR‴, —NR″C(O)NR‴R^p, —NR″S(O)_jR‴, —NR″S(O)_jNR‴R^p, a substituted or unsubstituted cycloalkyl ring, a substituted or unsubstituted heterocyclyl ring, a substituted or unsubstituted aryl ring, and a substituted or unsubstituted heteroaryl ring;

$R^{13}$ is H or substituted or unsubstituted alkyl; $R^{14}$ is H or substituted or unsubstituted alkyl;

$R^{15}$ is H, substituted or unsubstituted alkyl, halide, —CN, —NO_2, —SR‴, —OR‴, —NR‴R″, —C(O)R‴, —C(O)OR‴, —C(O)NR‴R″, —S(O)_jR‴, —S(O)_jNR‴R″, —NR″C(O)R‴, —NR″C(O)OR‴, —NR″C(O)NR‴R^p, —NR″S(O)_jR‴, —NR″S(O)_jNR‴R^p, a substituted or unsubstituted cycloalkyl ring, a substituted or unsubstituted heterocyclyl ring, a substituted or unsubstituted aryl ring, or a substituted or unsubstituted heteroaryl ring;

$R^{16}$ is aryl or heteroaryl;

each $R^{17}$ is independently selected from the group consisting of substituted or unsubstituted alkyl, halide, —CN, —NO_2, —SR‴, —OR‴, —NR‴R″, —C(O)R‴, —C(O)OR‴, —C(O)NR‴R″, —S(O)_jR‴, —S(O)_jNR‴R″, —NR″C(O)R‴, —NR″C(O)OR‴, —NR″C(O)NR‴R^p, —NR″S(O)_jR‴, —NR″S(O)_jNR‴R^p, a substituted or unsubstituted cycloalkyl ring, a substituted or unsubstituted heterocyclyl ring, a substituted or unsubstituted aryl ring, and a substituted or unsubstituted heteroaryl ring;

$R^{18}$ is H, substituted or unsubstituted alkyl, —C(O)R‴, —C(O)OR‴, —C(O)NR‴R″, —S(O)_jR‴, —S(O)_jNR‴R″, a substituted or unsubstituted cycloalkyl ring, a substituted or unsubstituted heterocyclyl ring, a substituted or unsubstituted aryl ring, or a substituted or unsubstituted heteroaryl ring;

$R^{19}$ is H, substituted or unsubstituted alkyl, halide, —CN, —NO_2, —SR‴, —OR‴, —NR‴R″, —C(O)R‴, —C(O)OR‴, —C(O)NR‴R″, —S(O)_jR‴, —S(O)_jNR‴R″, —NR″C(O)R‴, —NR″C(O)OR‴, —NR″C(O)NR‴R^p, —NR″S(O)_jR‴, —NR″S(O)_jNR‴R^p, a substituted or unsubstituted cycloalkyl ring, a substituted or unsubstituted heterocyclyl ring, a substituted or unsubstituted aryl ring, or a substituted or unsubstituted heteroaryl ring;

Q is —SO_2— or —C(O)—;

W is S, substituted or unsubstituted alkyl, a substituted or unsubstituted aryl ring, or a substituted or unsubstituted heteroaryl ring;

X is O or S;

each $R'''$, $R''$, and $R^p$ is independently selected from the group consisting of H, substituted or unsubstituted alkyl, a substituted or unsubstituted cycloalkyl ring, a substituted or unsubstituted heterocyclyl ring, a substituted or unsubstituted aryl ring, and a substituted or unsubstituted heteroaryl ring;

b is 0 or 1; j is 1 or 2; k is 0, 1, 2, 3, 4 or 5; m is 0, 1, 2, 3, or 4; n is 0, 1, 2, 3, 4, or 5; p is 0, 1, 2, 3, 4, or 5; q is 0, 1, 2, 3, 4, or 5; r is 1, 2, 3, 4, or 5; s is 1, 2, 3, 4, or 5; and t is 1, 2, 3, 4, or 5.

In some embodiments, the contacting of the macrophage is performed in an in vitro assay. In some embodiments, the contacting of the macrophage is performed in an in vivo assay. In one aspect, an effective amount, e.g., a therapeutically effective amount is contacted.

In some embodiments of the methods described herein, the compound of Formula I, Formula II, Formula III, Formula IV, Formula V or a stereoisomer, tautomer, or pharmaceutically acceptable salt thereof, is selected from the group consisting of

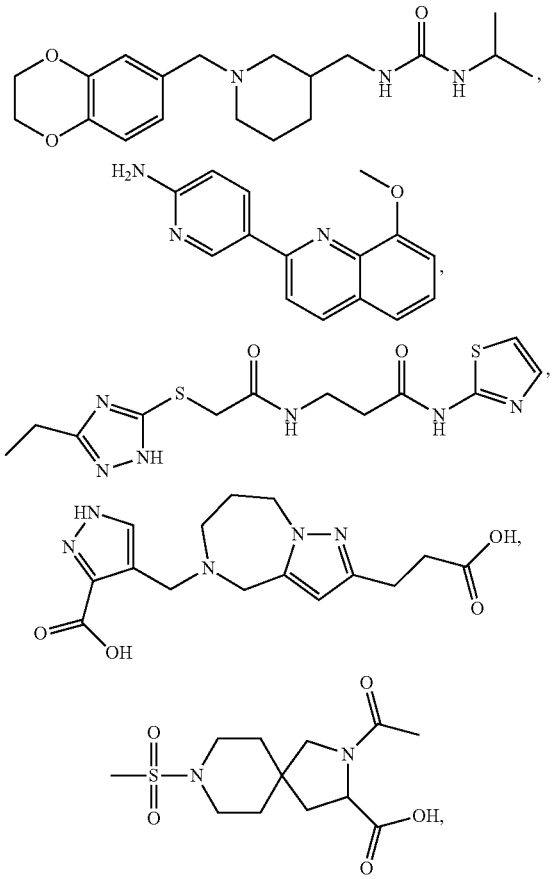

-continued

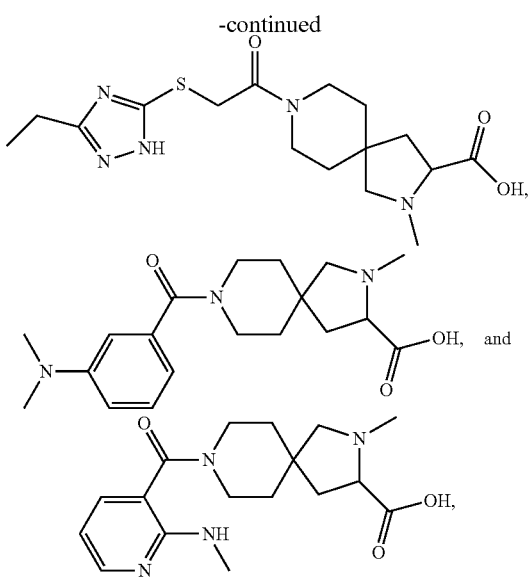

or a stereoisomer, tautomer, or pharmaceutically acceptable salt thereof.

Provided herein in another aspect are methods to inhibit the growth of a cancer cell or to treat cancer or inflammatory disease in a subject in need thereof, the methods comprising, or alternatively consisting essentially of, or yet further consisting of, administering to the cell or subject a compound selected from the group consisting of:

1-acetyl-4-{[1-(2-chlorophenyl)-1H-pyrazol-4-yl]methyl}-1,4-diazepan-6-ol;
2-{1-[1-(3-pyridinylmethyl)-4-piperidinyl]-1H-1,2,3-triazol-4-yl}ethanol;
1-(1-{[1-(1,3-thiazol-4-ylcarbonyl)-4-piperidinyl]methyl}-1H-1,2,3-triazol-4-yl)ethanol;
2-acetyl-8-(methylsulfonyl)-2,8-diazaspiro[4.5]decane-3-carboxylic acid;
5-[(4-pyridin-2-ylpiperazin-1-yl)carbonyl]-1H-imidazole-4-carboxylic acid;
8-{[(3-ethyl-1H-1,2,4-triazol-5-yl)thio]acetyl}-2-methyl-2,8-diazaspiro[4.5]decane-3-carboxylic acid;
8-[3-(dimethylamino)benzoyl]-2-methyl-2,8-diazaspiro[4.5]decane-3-carboxylic acid;
2-methyl-8-{[2-(methylamino)-3-pyridinyl]carbonyl}-2,8-diazaspiro[4.5]decane-3-carboxylic acid;
N-[2-(2-amino-1,3-thiazol-4-yl)ethyl]-5-ethyl-2,3-dimethylpyrazolo[1,5-a]pyrimidin-7-amine
N-[(5-acetyl-5,6,7,8-tetrahydro-4H-pyrazolo[1,5-a][1,4]diazepin-2-yl)methyl]-1,3-benzothiazol-2-amine;
N-[(1,5-dimethyl-1H-indazol-3-yl)methyl]-N'-(1-propyl-1H-1,2,3-triazol-4-yl)urea;
N-{[1-(2,3-dihydro-1,4-benzodioxin-6-ylmethyl)piperidin-3-yl]methyl}-N'-isopropylurea;
5-(8-methoxyquinolin-2-yl)pyridin-2-amine; and
3-({[(3-ethyl-1H-1,2,4-triazol-5-yl)thio]acetyl}amino)-N-1,3-thiazol-2-ylpropanamide;

or a stereoisomer, tautomer, or pharmaceutically acceptable salt thereof. In one aspect, an effective amount or a therapeutically effective amount of the compound is administered to the cell or subject.

In some embodiments of the methods to treat the cancer cell or the cancer, the cancer is selected from heart sarcoma, lung cancer, small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; cancer of the gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); cancer of the genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); cancer of the liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); cancer of bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; cancer of the nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiforme, oligodendroglioma, schwannoma, retinoblastoma, congenital tumors), spinal cord neurofibroma, meningioma, glioma, sarcoma); cancer of the reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; cancer of the hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; cancer of the oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; cancer of the skin, for example, malignant melanoma, cutaneous melanoma, basal cell carcinoma, squamous cell carcinoma, Karposi's sarcoma, moles dysplastic nevi, lipoma, angioma, dermatofibroma, and keloids; cancer of the adrenal glands: neuroblastoma; and cancer of other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

Provided herein in another aspect are methods to stimulate M1 macrophage polarization, the method comprising, or alternatively consisting essentially of, or yet further consisting of contacting a macrophage with a compound selected from the group consisting of:

1-acetyl-4-{[1-(2-chlorophenyl)-1H-pyrazol-4-yl]methyl}-1,4-diazepan-6-ol;
2-{1-[1-(3-pyridinylmethyl)-4-piperidinyl]-1H-1,2,3-triazol-4-yl}ethanol;
1-(1-{[1-(1,3-thiazol-4-ylcarbonyl)-4-piperidinyl]methyl}-1H-1,2,3-triazol-4-yl)ethanol;
2-acetyl-8-(methylsulfonyl)-2,8-diazaspiro[4.5]decane-3-carboxylic acid;
5-[(4-pyridin-2-ylpiperazin-1-yl)carbonyl]-1H-imidazole-4-carboxylic acid;
8-{[(3-ethyl-1H-1,2,4-triazol-5-yl)thio]acetyl}-2-methyl-2,8-diazaspiro[4.5]decane-3-carboxylic acid;
8-[3-(dimethylamino)benzoyl]-2-methyl-2,8-diazaspiro[4.5]decane-3-carboxylic acid;
2-methyl-8-{[2-(methylamino)-3-pyridinyl]carbonyl}-2,8-diazaspiro[4.5]decane-3-carboxylic acid;
N-[2-(2-amino-1,3-thiazol-4-yl)ethyl]-5-ethyl-2,3-dimethylpyrazolo[1,5-a]pyrimidin-7-amine
N-[(5-acetyl-5,6,7,8-tetrahydro-4H-pyrazolo[1,5-a][1,4]diazepin-2-yl)methyl]-1,3-benzothiazol-2-amine;
N-[(1,5-dimethyl-1H-indazol-3-yl)methyl]-N'-(1-propyl-1H-1,2,3-triazol-4-yl)urea;
N-{[1-(2,3-dihydro-1,4-benzodioxin-6-ylmethyl)piperidin-3-yl]methyl}-N'-isopropylurea;
5-(8-methoxyquinolin-2-yl)pyridin-2-amine; and
3-({[(3-ethyl-1H-1,2,4-triazol-5-yl)thio]acetyl}amino)-N-1,3-thiazol-2-ylpropanamide;

or a stereoisomer, tautomer, or pharmaceutically acceptable salt thereof.

In some embodiments, the contacting of the macrophage is performed in an in vitro assay. In some embodiments, the contacting of the macrophage is performed in an in vivo assay. In one aspect, an effective amount, e.g., a therapeutically effective amount is contacted with the macrophage/

Provided herein in another aspect are methods to inhibit M2 macrophage polarization, the method comprising or alternatively consisting essentially of, or yet further consisting of, contacting a macrophage with a compound selected from the group consisting of.

1-acetyl-4-{[1-(2-chlorophenyl)-1H-pyrazol-4-yl]methyl}-1,4-diazepan-6-ol;
2-{1-[1-(3-pyridinylmethyl)-4-piperidinyl]-1H-1,2,3-triazol-4-yl}ethanol;
1-(1-{[1-(1,3-thiazol-4-ylcarbonyl)-4-piperidinyl]methyl}-1H-1,2,3-triazol-4-yl)ethanol;
2-acetyl-8-(methylsulfonyl)-2,8-diazaspiro[4.5]decane-3-carboxylic acid;
5-[(4-pyridin-2-ylpiperazin-1-yl)carbonyl]-1H-imidazole-4-carboxylic acid;
8-{[(3-ethyl-1H-1,2,4-triazol-5-yl)thio]acetyl}-2-methyl-2,8-diazaspiro[4.5]decane-3-carboxylic acid;
8-[3-(dimethylamino)benzoyl]-2-methyl-2,8-diazaspiro[4.5]decane-3-carboxylic acid;
2-methyl-8-{[2-(methylamino)-3-pyridinyl]carbonyl}-2,8-diazaspiro[4.5]decane-3-carboxylic acid;
N-[2-(2-amino-1,3-thiazol-4-yl)ethyl]-5-ethyl-2,3-dimethylpyrazolo[1,5-a]pyrimidin-7-amine
N-[(5-acetyl-5,6,7,8-tetrahydro-4H-pyrazolo[1,5-a][1,4]diazepin-2-yl)methyl]-1,3-benzothiazol-2-amine;
N-[(1,5-dimethyl-1H-indazol-3-yl)methyl]-N'-(1-propyl-1H-1,2,3-triazol-4-yl)urea;
N-{[1-(2,3-dihydro-1,4-benzodioxin-6-ylmethyl)piperidin-3-yl]methyl}-N'-isopropylurea;
5-(8-methoxyquinolin-2-yl)pyridin-2-amine; and
3-({[(3-ethyl-1H-1,2,4-triazol-5-yl)thio]acetyl}amino)-N-1,3-thiazol-2-ylpropanamide;

or a stereoisomer, tautomer, or pharmaceutically acceptable salt thereof.

In some embodiments, the contacting of the macrophage is performed in an in vitro assay. In some embodiments, the contacting of the macrophage is performed in an in vivo assay. In one aspect, an effective amount is contacted, e.g., a therapeutically effective amount of the compound is contacted with the macrophage.

DETAILED DESCRIPTION

The present disclosure describes PI3Kγ inhibitors and methods of their use.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Definitions

As used herein, the term "alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In certain embodiments, an alkyl comprises one to three carbon atoms (e.g., $C_1$-$C_3$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. In some embodiments, a substituted alkyl group is an alkyl group substituted by one or more of the following substituents: halo, cyano, nitro, oxo, thioxo, —$OR^a$, —$SR^a$, —OC(O)—$R^b$, —N($R^a$)$_2$, —C(O)$R^a$, —C(O)O$R^a$, —C(O)N($R^a$)$_2$, —N($R^a$)C(O)O$R^a$, —N($R^a$)C(O)$R^a$, N($R^a$)S(O)$_2$$R^b$, —S(O)$_2$O$R^a$ and —S(O)$_2$N($R^a$)$_2$ where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl and each $R^b$ is independently alkyl, fluoroalkyl, carbocyclyl, carbocyclylalkyl, aryl, aralkyl, heterocyclyl, heterocyclylalkyl, heteroaryl or heteroarylalkyl.

The term "alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. In some embodiments, a substituted alkenyl group is an alkenyl group substituted by one or more of the following substituents: halo, cyano, nitro, oxo, thioxo, —OR$^a$, —SR$^a$, —OC(O)—R$^b$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_2$R$^b$, —S(O)$_2$OR$^a$ and —S(O)$_2$N(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl and each R$^b$ is independently alkyl, fluoroalkyl, carbocyclyl, carbocyclylalkyl, aryl, aralkyl, heterocyclyl, heterocyclylalkyl, heteroaryl or heteroarylalkyl.

The term "alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In certain embodiments, an alkynyl comprises two to six carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. In some embodiments, a substituted alkynyl group is an alkynyl group substituted by one or more of the following substituents: halo, cyano, nitro, oxo, thioxo, —OR$^a$, —SR$^a$, —OC(O)—R$^b$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_2$R$^b$, —S(O)$_2$OR$^a$ and —S(O)$_2$N(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl and each R$^b$ is independently alkyl, fluoroalkyl, carbocyclyl, carbocyclylalkyl, aryl, aralkyl, heterocyclyl, heterocyclylalkyl, heteroaryl or heteroarylalkyl.

The terms "alkylene" or "alkylene chain" refer to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. In some embodiments, an alkylene chain has one to six carbons. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In some embodiments, a substituted alkylene chain is an alkylene chain substituted by one or more of the following substituents: halo, cyano, nitro, oxo, thioxo, —OR$^a$, —SR$^a$, —OC(O)—R$^b$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_2$R$^b$, —S(O)$_2$OR$^a$ and —S(O)$_2$N(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl and each R$^b$ is independently alkyl, fluoroalkyl, carbocyclyl, carbocyclylalkyl, aryl, aralkyl, heterocyclyl, heterocyclylalkyl, heteroaryl or heteroarylalkyl.

The terms "alkenylene" or "alkenylene chain" refer to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. In some embodiments, an alkenylene chain has two to six carbons. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. In some embodiments, a substituted alkenylene chain is an alkenylene chain substituted by one or more of the following substituents: halo, cyano, nitro, oxo, thioxo, —OR$^a$, —SR$^a$, —OC(O)—R$^b$, —N(R$^a$)$_2$, —C(O)R$^a$, —C(O)OR$^a$, —C(O)N(R$^a$)$_2$, —N(R$^a$)C(O)OR$^a$, —N(R$^a$)S(O)$_2$R$^b$, —S(O)$_2$OR$^a$ and —S(O)$_2$N(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl and each R$^b$ is independently alkyl, fluoroalkyl, carbocyclyl, carbocyclylalkyl, aryl, aralkyl, heterocyclyl, heterocyclylalkyl, heteroaryl or heteroarylalkyl.

The terms "alkynylene" or "alkynylene chain" refer to a straight or branched divalent hydrocarbon chain linking the rest of the molecule to a radical group, consisting solely of carbon and hydrogen, containing at least one triple bond and having from two to twelve carbon atoms, for example, ethenylene, propenylene, n-butenylene, and the like. In some embodiments, an alkynylene chain has two to six carbons. The alkynylene chain is attached to the rest of the molecule through a triple bond or a single bond and to the radical group through a triple bond or a single bond. The points of attachment of the alkynylene chain to the rest of the molecule and to the radical group can be through one carbon or any two carbons within the chain. In some embodiments, a substituted alkynylene chain is an alkenylene chain substituted by one or more of the following substituents: halo, cyano, nitro, oxo, thioxo, —OR$^a$, —SR$^a$, —OC(O)—R$^b$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_2$R$^b$, —S(O)$_2$OR$^a$ and —S(O)$_2$N(R$^a$)$_2$ where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl and each R$^b$ is independently alkyl, fluoroalkyl, carbocyclyl, carbocyclylalkyl, aryl, aralkyl, heterocyclyl, heterocyclylalkyl, heteroaryl or heteroarylalkyl.

The terms "aryl" or "aromatic moiety" refer to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. In some embodiments, aryl group has 6- to 10-carbon atoms. Aryl groups include, but are not limited to, groups such as phenyl, fluorenyl, and naphthyl. In some embodiments, a substituted aryl is an aryl substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—OC(O)—$R^b$, —$R^c$—$N(R^a)_2$, —$R^c$—C(O)$R^a$, —$R^c$—C(O)$OR^a$, —$R^c$—C(O)$N(R^a)_2$, —R—O—$R^d$—C(O)$N(R^a)_2$, —$R^c$—$N(R^a)$C(O)$OR^a$, —$R^c$—$N(R^a)$C(O)$R^a$, —$R^c$—$N(R^a)$S(O)$_2R^b$, —$R^c$—S(O)$_2OR^a$ and —$R^c$—S(O)$_2N(R^a)_2$, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, each $R^c$ is independently a direct bond or a straight or branched alkylene, alkenylene, or alkynylene chain, and $R^d$ is a straight or branched alkylene, alkenylene, or alkynylene chain, and where each of the above substituents is unsubstituted unless otherwise indicated.

The term "aralkyl" refers to a radical of the formula —$R^e$-aryl where $R^e$ is an alkylene chain as defined above, for example, benzyl, diphenylmethyl and the like.

The term "aralkenyl" refers to a radical of the formula —R-aryl where $R^f$ is an alkenylene chain as defined above.

The term "aralkynyl" refers to a radical of the formula —$R^g$-aryl, where $R^g$ is an alkynylene chain as defined above.

The term "carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In some embodiments, a carbocyclyl comprises five to seven carbon atoms. In some embodiments, a carbocyclyl comprises four to seven carbon atoms. In some embodiments, a carbocyclyl comprises five to six carbon atoms. The carbocyclyl is attached to the rest of the molecule by a single bond. Carbocyclyl may be saturated, (i.e., containing single C—C bonds only) or unsaturated (i.e., containing one or more double bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl,7,7-dimethyl-bicyclo[2.2.1]heptanyl, and the like. In some embodiments, a substituted carbocyclyl is a carbocyclyl substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—$SR^a$, —$R^c$—OC(O)—$R^b$, —$R^c$—$N(R^a)_2$, —$R^c$—C(O)$R^a$, —$R^c$—C(O)$OR^a$, —$R^c$—C(O)$N(R^a)_2$, —$R^c$—O—$R^d$—C(O)$N(R^a)_2$, —$R^c$—$N(R^a)$C(O)$OR^a$, —$R^c$—$N(R^a)$C(O)$R^a$, —$R^c$—$N(R^a)$S(O)$_2R^b$, —$R^c$—S(O)$_2OR^a$ and —$R^c$—S(O)$_2N(R^a)_2$ where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, and each $R^c$ is independently a direct bond or a straight or branched alkylene, alkenylene, or alkynylene chain.

The term "carbocyclylalkyl" refers to a radical of the formula —$R^e$-carbocyclyl where $R^e$ is an alkylene chain as defined above.

The term "fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like.

The term "heterocyclyl" refers to a stable 4- to 18-membered non-aromatic ring radical that comprises three to twelve carbon atoms and from one to six heteroatoms selected from nitrogen, oxygen and sulfur. In some embodiments, a heterocyclyl is a 5- to 6-membered non-aromatic ring radical comprising one to three heteroatoms independently selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. In some embodiments, one or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. In some embodiments, a substituted heterocyclyl is a heterocyclyl substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—$SR^a$, —$R^c$—OC(O)—$R^b$, —$R^c$—$N(R^a)_2$, —$R^c$—C(O)$R^a$, —$R^c$—C(O)$OR^a$, —$R^c$—C(O)$N(R^a)_2$, —$R^c$—O—$R^d$—C(O)$N(R^a)_2$, —$R^c$—$N(R^a)$C(O)$OR^a$, —$R^c$—$N(R^a)$C(O)$R^a$, —$R^c$—$N(R^a)$S(O)$_2R^b$, —$R^c$—S(O)$_2OR^a$ and —$R^c$—S(O)$_2N(R^a)_2$, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, and each $R^c$ is independently a direct bond or a straight or branched alkylene, alkenylene, or alkynylene chain.

The term "non-aromatic cyclic moiety" refers to a carbocyclyl or heterocyclyl radical as defined above. In some embodiments, a non-aromatic cyclic moiety is selected from a carbocyclyl radical as defined above and a heterocyclyl radical as defined above. In some embodiments, a non-aromatic cyclic moiety is a carbocyclyl radical as defined above. In some embodiments, a non-aromatic cyclic moiety is a heterocyclyl radical as defined above.

The term "heterocyclylalkyl" refers to a radical of the formula —$R^e$-heterocyclyl where $R^e$ is an alkylene chain as defined above. If the heterocyclyl is a nitrogen-containing heterocyclyl, the heterocyclyl is optionally attached to the alkyl radical at the nitrogen atom.

The term "heteroaryl" refers to a radical derived from a 5- to 18-membered aromatic ring radical that comprises one to seventeen carbon atoms and from one to six heteroatoms selected from nitrogen, oxygen and sulfur. In some embodiments, a heteroaryl is a 5- to 6-membered aromatic ring radical comprising one to three ring heteroatoms independently selected from nitrogen, oxygen, and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) 7-electron system in accordance with the Hückel theory. Heteroaryl includes fused or bridged ring systems. In some embodiments, the heteroatom(s) in the heteroaryl radical is optionally oxidized. In some embodiments, one or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). In some embodiments, a substituted heteroaryl is a heteroaryl substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^c$—$OR^a$, —$R^c$—$SR^a$, —$R^c$—OC(O)—$R^b$, —$R^c$—$N(R^a)_2$, —$R^c$—C(O)$R^a$, —$R^c$—C(O)$OR^a$, —$R^c$—C(O)$N(R^a)_2$, —$R^c$—$OR^d$—C(O)$N(R^a)_2$, —$R^c$—N($R^a$)C(O)$OR^a$, —$R^c$—N($R^a$)C(O)$R^a$, —$R^c$—N($R^a$)S(O)$_2R^b$, —$R^c$—S(O)$_2OR^a$ and —$R^c$—S(O)$_2N(R^a)_2$, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently alkyl, fluoroalkyl, carbocyclyl, carbocyclylalkyl, aryl, aralkyl, heterocyclyl, heterocyclylalkyl, heteroaryl or heteroarylalkyl, and each $R^c$ is independently a direct bond or a straight or branched alkylene, alkenylene, or alkynylene chain.

The term "aromatic moiety" refers to an aryl or heteroaryl radical as defined above. In some embodiments, an aromatic moiety is an aryl radical as defined above. In some embodiments, an aromatic moiety is a heteroaryl radical as defined above. In some embodiments, an aromatic moiety is selected from an aryl radical as defined above and a heteroaryl radical as defined above.

The term "heteroarylalkyl" refers to a radical of the formula —$R^e$-heteroaryl, where $R^e$ is an alkylene chain as defined above. In some embodiments, the heteroaryl is a nitrogen-containing heteroaryl, and the heteroaryl is optionally attached to the alkyl radical at the nitrogen atom.

The term "cyano" refers to the —CN radical.

The term "oxo" refers to the =O radical.

The term "thioxo" refers to the =S radical.

The terms "optional" or "optionally" mean that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached. The term "epimer" refers to diastereomers that have opposite configuration at only one of two or more tetrahedral stereogenic centers present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

As used herein, the term "tautomers" refers to particular isomers of a compound in which a hydrogen and double bond have changed position with respect to the other atoms of the molecule. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridione-hydroxypyridine forms.

The term "racemic" refers to a mixture of equal parts of enantiomers and which mixture is optically inactive.

The term "resolution" refers to the separation or concentration or depletion of one of the two enantiomeric forms of a molecule.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

"Therapeutically effective amount" of a drug or an agent refers to an amount of the drug or the agent that is an amount sufficient to obtain a pharmacological response such as inhibiting a biological target; or alternatively, is an amount of the drug or agent that, when administered to a patient with a specified disorder or disease, is sufficient to have the intended effect, e.g., treatment, alleviation, amelioration, palliation or elimination of one or more manifestations of the specified disorder or disease in the patient. A therapeutic effect does not necessarily occur by administration of one dose, and may occur only after administration of a series of doses. Thus, a therapeutically effective amount may be administered in one or more administrations.

As used herein, the term "administration" and "administering" are used to mean introducing an agent into a subject. Routes of administration include, but are not limited to, oral (such as a tablet, capsule or suspension), topical, transdermal, intranasal, vaginal, rectal, subcutaneous intravenous, intravenous, intraarterial, intramuscular, intraosseous, intraperitoneal, intraocular, subconjunctival, sub-Tenon's, intravitreal, retrobulbar, intracameral, intratumoral, epidural and intrathecal.

Compounds

In one aspect, disclosed herein are compounds of Formula I, Formula II, Formula III, Formula IV, or Formula V, or a stereoisomer, tautomer, or pharmaceutically acceptable salt thereof:

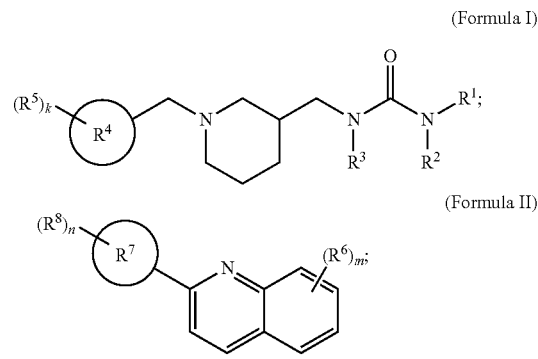

(Formula I)

(Formula II)

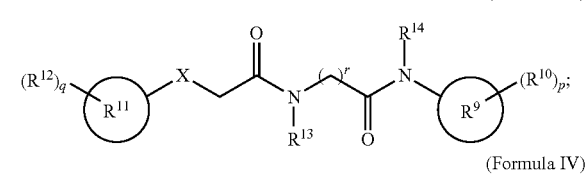

(Formula III)

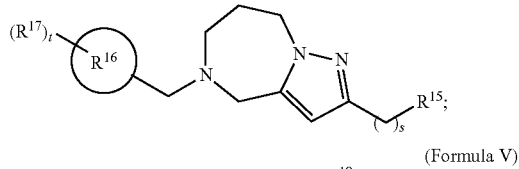

(Formula IV)

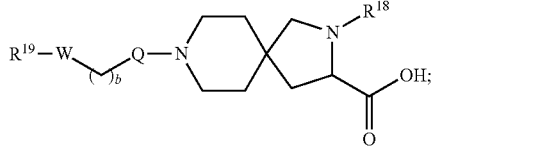

(Formula V)

wherein $R^1$ is H or substituted or unsubstituted alkyl; $R^2$ is H or substituted or unsubstituted alkyl;

$R^3$ is H or substituted or unsubstituted alkyl; $R^4$ is aryl or heteroaryl;

each $R^5$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring; or two adjacent $R^5$, together with the atoms to which they are attached, form a substituted or unsubstituted cycloalkyl ring, a substituted or unsubstituted heterocyclyl ring, a substituted or unsubstituted aryl ring, or a substituted or unsubstituted heteroaryl ring;

each $R^6$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^7$ is aryl or heteroaryl;

each $R^8$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^9$ is aryl or heteroaryl;

each $R^{10}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{11}$ is aryl or heteroaryl;

each $R^{12}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{13}$ is H or substituted or unsubstituted alkyl; $R^{14}$ is H or substituted or unsubstituted alkyl;

$R^{15}$ is H, substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, or a substituted or unsubstituted heteroaryl ring;

$R^{16}$ is aryl or heteroaryl;

each $R^{17}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{18}$ is H, substituted or unsubstituted alkyl, —C(O)R$^m$, —C(O)OR$^m$, —C(O)NR$^m$R$^n$, —S(O)$_j$R$^m$, —S(O)$_j$NR$^m$R$^n$, a substituted or unsubstituted cycloalkyl ring, a substituted or unsubstituted heterocyclyl ring, a substituted or unsubstituted aryl ring, or a substituted or unsubstituted heteroaryl ring;

$R^{19}$ is H, substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, or a substituted or unsubstituted heteroaryl ring;

Q is —SO$_2$— or —C(O)—;

W is S, substituted or unsubstituted alkyl, a substituted or unsubstituted aryl ring, or a substituted or unsubstituted heteroaryl ring;

X is O or S;

each $R^m$, $R^n$, and $R^p$ is independently selected from the group consisting of H, substituted or unsubstituted alkyl, a substituted or unsubstituted cycloalkyl ring, a substituted or unsubstituted heterocyclyl ring, a substituted or unsubstituted aryl ring, and a substituted or unsubstituted heteroaryl ring b is 0 or 1; j is 1 or 2; k is 0, 1, 2, 3, 4 or 5; m is 0, 1, 2, 3, or 4; n is 0, 1, 2, 3, 4, or 5; p is 0, 1, 2, 3, 4, or 5; q is 0, 1, 2, 3, 4, or 5; r is 1, 2, 3, 4, or 5; s is 1, 2, 3, 4, or 5; and t is 1, 2, 3, 4, or 5.

In some embodiments, the compound is of Formula I wherein:

$R^1$ is H or substituted or unsubstituted $C_1$-$C_6$ alkyl; $R^2$ is H or substituted or unsubstituted $C_1$-$C_6$ alkyl; $R^3$ is H or substituted or unsubstituted $C_1$-$C_6$ alkyl; $R^4$ is aryl;

each $R^5$ is independently selected from the group consisting of substituted or unsubstituted $C_1$-$C_6$ alkyl, halide, —CN, —NO$_2$, —SR$^m$, —OR$^m$, and —NR$^m$R$^n$, or two adjacent $R^5$, together with the atoms to which they are attached, form a substituted or unsubstituted 5- or 6-membered heterocyclyl ring;

each $R^m$ and $R^n$ is independently H or substituted or unsubstituted $C_1$-$C_6$ alkyl; and k is 0, 1, or 2.

In some embodiments, $R^4$ is phenyl.

In some embodiments, $R^1$ is H or $C_1$-$C_6$ alkyl. In some embodiments, $R^1$ is H or $C_1$-$C_3$ alkyl. In some embodiments, $R^2$ is H or $C_1$-$C_6$ alkyl. In some embodiments, $R^3$ is H or $C_1$-$C_6$ alkyl. In some embodiments, $R^2$ is H and $R^3$ is H.

In some embodiments, the compound is of Formula I wherein:

$R^1$ is H or unsubstituted $C_1$-$C_6$ alkyl; $R^2$ is H or unsubstituted $C_1$-$C_6$ alkyl; $R^3$ is H or unsubstituted $C_1$-$C_6$ alkyl; $R^4$ is phenyl;

each $R^5$ is independently selected from the group consisting of substituted or unsubstituted $C_1$-$C_6$ alkyl, halide, —CN, —NO$_2$, —SCH$_3$, —OCH$_3$, and —NH$_2$, or two adjacent R$^5$, together with the atoms to which they are attached, form a substituted or unsubstituted 5- or 6-membered heterocyclyl ring; and k is 0, 1, or 2.

In some embodiments, the compound is of Formula I wherein:

R$^1$ is H or unsubstituted C$_1$-C$_6$ alkyl; R$^2$ is H; R$^3$ is H; R$^4$ is phenyl;

each R$^5$ is independently selected from the group consisting of substituted or unsubstituted C$_1$-C$_6$ alkyl, halide, —CN, —NO$_2$, —SCH$_3$, —OCH$_3$, and —NH$_2$, or two adjacent R$^5$, together with the atoms to which they are attached, form a substituted or unsubstituted 5- or 6-membered heterocyclyl ring; and k is 0, 1, or 2.

In some embodiments, the compound is of Formula II wherein:

each R$^6$ is independently selected from the group consisting of substituted or unsubstituted C$_1$-C$_6$ alkyl, halide, —CN, —NO$_2$, —SR$^m$, —OR$^m$, and —NR$^m$R$^n$;

R$^7$ is heteroaryl;

each R$^8$ is independently selected from the group consisting of substituted or unsubstituted C$_1$-C$_6$ alkyl, halide, —CN, —NO$_2$, —SR$^m$, —OR$^m$, and —NR$^m$R$^n$;

each R$^m$ and R$^n$ is independently H or substituted or unsubstituted C$_1$-C$_6$ alkyl;

m is 0, 1, or 2; and n is 0, 1, or 2.

In some embodiments, R$^7$ is pyridinyl.

In some embodiments, n is 1. In some embodiments, m is 1. In some embodiments, n and m are both 1.

In some embodiments, each R$^m$ and R$^n$ is independently H or unsubstituted C$_1$-C$_6$ alkyl.

In some embodiments, each R$^6$ is independently selected from the group consisting of unsubstituted C$_1$-C$_6$ alkyl, halide, —CN, —NO$_2$, —SR$^m$, —OR$^m$, and —NR$^m$R$^n$. In some embodiments, R$^6$ is unsubstituted C$_1$-C$_6$ alkyl. In some embodiments, R$^6$ is halide. In some embodiments, R$^6$ is —CN. In some embodiments, R$^6$ is —NO$_2$. In some embodiments, R$^6$ is —SR$^m$. In some embodiments, R$^6$ is —OR$^m$. In some embodiments, R$^6$ is —NR$^m$R$^n$. In some embodiments, R$^6$ is —NH$_2$.

In some embodiments, each R$^8$ is independently selected from the group consisting of unsubstituted C$_1$-C$_6$ alkyl, halide, —CN, —NO$_2$, —SR$^m$, —OR$^m$, and —NR$^m$R$^n$. In some embodiments, R$^8$ is unsubstituted C$_1$-C$_6$ alkyl. In some embodiments, R$^8$ is halide. In some embodiments, R$^8$ is —CN. In some embodiments, R$^8$ is —NO$_2$. In some embodiments, R$^8$ is —SR$^m$. In some embodiments, R$^8$ is —OR$^m$. In some embodiments, R$^8$ is —OCH$_3$. In some embodiments, R$^8$ is —NR$^m$R$^n$.

In some embodiments, the compound is of Formula II wherein:

each R$^6$ is independently selected from the group consisting of substituted or unsubstituted C$_1$-C$_6$ alkyl, halide, —CN, —NO$_2$, —SCH$_3$, —OCH$_3$, and —NH$_2$;

R$^7$ is pyridinyl;

each R$^8$ is independently selected from the group consisting of substituted or unsubstituted C$_1$-C$_6$ alkyl, halide, —CN, —NO$_2$, —SCH$_3$, —OCH$_3$, and —NH$_2$;

m is 1; and n is 1.

In some embodiments, the compound is of Formula III wherein:

R$^9$ is heteroaryl;

each R$^{10}$ is independently selected from the group consisting of substituted or unsubstituted C$_1$-C$_6$ alkyl, halide, —CN, —NO$_2$, —SR$^m$, —OR$^m$, and —NR$^m$R$^n$;

R$^{11}$ is heteroaryl;

each R$^{12}$ is independently selected from the group consisting of substituted or unsubstituted C$_1$-C$_6$ alkyl, halide, —CN, —NO$_2$, —SR$^m$, —OR$^m$, and —NR$^m$R$^n$;

R$^{13}$ is H or substituted or unsubstituted C$_1$-C$_6$ alkyl;

R$^{14}$ is H or substituted or unsubstituted C$_1$-C$_6$ alkyl;

each R$^m$ and R$^n$ is independently H or substituted or unsubstituted C$_1$-C$_6$ alkyl;

X is O or S; p is 0, 1, or 2; q is 0, 1, or 2; and r is 1, 2, 3, 4, or 5.

In some embodiments, R$^9$ is thiazolyl.

In some embodiments, R$^{11}$ is 1,2,4-triazolyl.

In some embodiments, X is S. In some embodiments, X is O.

In some embodiments, p is 0. In some embodiments, p is 1. In some embodiments, p is 2. In some embodiments, q is 0. In some embodiments, q is 1. In some embodiments, q is 2. In some embodiments, r is 1. In some embodiments, r is 2. In some embodiments, r is 3. In some embodiments, r is 4. In some embodiments, r is 5. In some embodiments, p is 0, r is 2, and q is 1.

In some embodiments, each R$^{10}$ is independently selected from the group consisting of unsubstituted C$_1$-C$_6$ alkyl, halide, —CN, —NO$_2$, —SR$^m$, —OR$^m$, and —NR$^m$R$^n$. In some embodiments, R$^{10}$ is unsubstituted C$_1$-C$_6$ alkyl. In some embodiments, R$^{10}$ is halide. In some embodiments, R$^{10}$ is —CN. In some embodiments, R$^{10}$ is —NO$_2$. In some embodiments, R$^{10}$ is —SR$^m$. In some embodiments, R$^{10}$ is —OR$^m$. In some embodiments, R$^{10}$ is —NR$^m$R$^n$.

In some embodiments, each R$^{12}$ is independently selected from the group consisting of unsubstituted C$_1$-C$_6$ alkyl, halide, —CN, —NO$_2$, —SR$^m$, —OR$^m$, and —NR$^m$R$^n$. In some embodiments, R$^{12}$ is unsubstituted C$_1$-C$_6$ alkyl. In some embodiments, R$^{12}$ is halide. In some embodiments, R$^{12}$ is —CN. In some embodiments, R$^{12}$ is —NO$_2$. In some embodiments, R$^{12}$ is —SR$^m$. In some embodiments, R$^{12}$ is —OR$^m$. In some embodiments, R$^{12}$ is —NR$^m$R$^n$.

In some embodiments, R$^{13}$ is H or unsubstituted C$_1$-C$_6$ alkyl. In some embodiments, R$^{13}$ is H. In some embodiments, R$^{13}$ is unsubstituted C$_1$-C$_6$ alkyl.

In some embodiments, R$^{14}$ is H or unsubstituted C$_1$-C$_6$ alkyl. In some embodiments, R$^{14}$ is H. In some embodiments, R$^{14}$ is unsubstituted C$_1$-C$_6$ alkyl.

In some embodiments, R$^{13}$ and R$^{14}$ are both H.

In some embodiments, the compound is of Formula III wherein:

R$^9$ is thiazolyl;

each R$^{10}$ is independently selected from the group consisting of substituted or unsubstituted C$_1$-C$_6$ alkyl, halide, —CN, —NO$_2$, —SCH$_3$, —OCH$_3$, and —NH$_2$;

R$^{11}$ is 1,2,4-triazolyl;

each R$^{12}$ is independently selected from the group consisting of substituted or unsubstituted C$_1$-C$_6$ alkyl, halide, —CN, —NO$_2$, —SCH$_3$, —OCH$_3$, and —NH$_2$;

R$^{13}$ is H or unsubstituted C$_1$-C$_6$ alkyl; R$^{14}$ is H or unsubstituted C$_1$-C$_6$ alkyl;

X is O or S; p is 0, 1, or 2; q is 0, 1, or 2; and r is 2.

In some embodiments, the compound is of Formula III wherein:

R$^9$ is thiazolyl;

each R$^{10}$ is independently selected from the group consisting of substituted or unsubstituted C$_1$-C$_6$ alkyl, halide, —CN, —NO$_2$, —SCH$_3$, —OCH$_3$, and —NH$_2$;

R$^{11}$ is 1,2,4-triazolyl;

each R$^{12}$ is independently selected from the group consisting of substituted or unsubstituted C$_1$-C$_6$ alkyl, halide, —CN, —NO$_2$, —SCH$_3$, —OCH$_3$, and —NH$_2$;

$R^{13}$ is H; $R^{14}$ is H; X is or S; p is 0, 1, or 2; q is 0, 1, or 2; and r is 2.

In some embodiments, the compound is of Formula IV wherein:
$R^{15}$ is —C(O)OR′′′, —C(O)NR′′′R′′, —S(O)$_j$R′′′, —S(O)$_j$NR′′′R′′, —NR′′C(O)R′′′, —NR′′C(O)OR′′′, —NR′′C(O)NR′′′R$^p$, —NR′′S(O)$_j$R′′′, or —NR′′S(O)$_j$NR′′′R$^p$;
$R^{16}$ is heteroaryl;
each $R^{17}$ is independently selected from the group consisting of substituted or unsubstituted $C_1$-$C_6$ alkyl, halide, —CN, —NO$_2$, —SR′′′, —OR′′′, —NR′′′R′′, —C(O)R′′′, —C(O)OR′′′, —C(O)NR′′′R′′, —S(O)$_j$R′′′, and —S(O)$_j$NR′′′R′′;
each R′′′, R′′, and R$^p$ is independently H or substituted or unsubstituted $C_1$-$C_6$ alkyl;
j is 1 or 2; s is 1, 2, or 3; and t is 1, 2, or 3.

In some embodiments, $R^{16}$ is pyrazolyl.

In some embodiments, $R^{15}$ is —C(O)OR′′′. In some embodiments, $R^{15}$ is —C(O)OH. In some embodiments, $R^{15}$ is —C(O)NR′′′R′′. In some embodiments, $R^{15}$ is —S(O)$_j$R′′′. In some embodiments, $R^{15}$ is —S(O)$_j$NR′′′R′′. In some embodiments, $R^{15}$ is —NR′′C(O)R′′′. In some embodiments, $R^{15}$ is —NR′′C(O)OR′′′. In some embodiments, $R^{15}$ is —NR′′C(O)NR′′′R$^p$. In some embodiments, $R^{15}$ is —NR′′S(O)$_j$R′′′. In some embodiments, $R^{15}$ is —NR′′S(O)$_j$NR′′′R$^p$.

In some embodiments, j is 1. In some embodiments, j is 2.

In some embodiments, s is 1. In some embodiments, s is 2. In some embodiments, s is 3.

In some embodiments, t is 1. In some embodiments, t is 2. In some embodiments, t is 3.

In some embodiments, $R^{17}$ is unsubstituted $C_1$-$C_6$ alkyl, halide, —CN, —NO$_2$, —SR′′′, —OR′′′, —NR′′′R′′, —C(O)R′′′, —C(O)OR′′′, —C(O)NR′′′R′′, —S(O)$_j$R′′′, or —S(O)$_j$NR′′′R′′. In some embodiments, $R^{17}$ is unsubstituted $C_1$-$C_6$ alkyl. In some embodiments, $R^{17}$ is halide. In some embodiments, $R^{17}$ is —CN. In some embodiments, $R^{17}$ is —NO$_2$. In some embodiments, $R^{17}$ is —SR′′′. In some embodiments, $R^{17}$ is —OR′′′. In some embodiments, $R^{17}$ is —NR′′′R′′. In some embodiments, $R^{17}$ is —C(O)R′′′. In some embodiments, $R^{17}$ is —C(O)OR′′′. In some embodiments, $R^{17}$ is —C(O)OH. In some embodiments, $R^{17}$ is —C(O)NR′′′R′′. In some embodiments, $R^{17}$ is —S(O)$_j$R′′′. In some embodiments, $R^{17}$ is —S(O)$_j$NR′′′R′′.

In some embodiments, the compound is of Formula IV wherein:
$R^{15}$ is —C(O)OR′′′ or —C(O)NR′′′R′′; $R^{16}$ is pyrazolyl;
each $R^{17}$ is independently selected from the group consisting of substituted or unsubstituted $C_1$-$C_6$ alkyl, halide, —CN, —NO$_2$, —SCH$_3$, —OCH$_3$, —NH$_2$, —C(O)R′′′, —C(O)OR′′′, or —C(O)NR′′′R′′;
each R′′′ and R′′ is independently H or unsubstituted $C_1$-$C_6$ alkyl; s is 1, 2, or 3; and t is 1, 2, or 3.

In some embodiments, the compound is of Formula V wherein:
$R^{18}$ is substituted or unsubstituted $C_1$-$C_6$ alkyl, —C(O)R′′′, —C(O)OR′′′, —C(O)NR′′′R′′, —S(O)$_j$R′′′, or —S(O)$_j$NR′′′R′′;
$R^{19}$ is H, substituted or unsubstituted $C_1$-$C_6$ alkyl, halide, —CN, —NO$_2$, —SR′′′, —OR′′′, —NR′′′R′′, or a substituted or unsubstituted heteroaryl ring;
each R′′′ and R′′ is independently H or substituted or unsubstituted $C_1$-$C_6$ alkyl;
Q is —SO$_2$— or —C(O)—;
W is S, substituted or unsubstituted $C_1$-$C_6$ alkyl, a substituted or unsubstituted aryl ring, or a substituted or unsubstituted heteroaryl ring; b is 0 or 1; and j is 1 or 2.

In some embodiments, $R^{18}$ is substituted or unsubstituted $C_1$-$C_6$ alkyl. In some embodiments, $R^{18}$ is —C(O)R′′′. In some embodiments, $R^{18}$ is —C(O)OR′′′. In some embodiments, $R^{18}$ is —C(O)NR′′′R′′. In some embodiments, $R^{18}$ is —S(O)$_j$R′′′. In some embodiments, $R^{18}$ is —S(O)$_j$NR′′′R′′. In some embodiments, $R^{18}$ is substituted or unsubstituted $C_1$-$C_6$ alkyl or —C(O)R′′′. In some embodiments, $R^{18}$ is unsubstituted $C_1$-$C_6$ alkyl or —C(O)R′′′. In some embodiments, $R^{18}$ is unsubstituted $C_1$-$C_6$ alkyl or —C(O)CH$_3$.

In some embodiments, $R^{19}$ is H, unsubstituted $C_1$-$C_6$ alkyl, halide, —CN, —NO$_2$, —SR′′′, —OR′′′, —NR′′′R′′, or a substituted or unsubstituted heteroaryl ring. In some embodiments, $R^{19}$ is H. In some embodiments, $R^{19}$ is unsubstituted $C_1$-$C_6$ alkyl. In some embodiments, $R^{19}$ is halide. In some embodiments, $R^{19}$ is —CN. In some embodiments, $R^{19}$ is —NO$_2$. In some embodiments, $R^{19}$ is —SR. In some embodiments, $R^{19}$ is —OR′′′. In some embodiments, $R^{19}$ is —NR′′′R′′. In some embodiments, $R^{19}$ is a substituted or unsubstituted heteroaryl ring. In some embodiments, $R^{19}$ is 1,2,4-triazolyl optionally substituted with $C_1$-$C_6$ alkyl. In some embodiments, $R^{19}$ is H, $C_1$-$C_6$ alkyl, —NR′′′R′′, or 1,2,4-triazolyl optionally substituted with $C_1$-$C_6$ alkyl.

In some embodiments, Q is —C(O)—. In some embodiments, Q is —SO$_2$—.

In some embodiments, W is S, an unsubstituted $C_1$-$C_6$ alkyl, an unsubstituted aryl ring, or an unsubstituted heteroaryl ring. In some embodiments, W is S. In some embodiments, W is an unsubstituted $C_1$-$C_6$ alkyl. In some embodiments, W is an unsubstituted aryl ring. In some embodiments, W is phenyl. In some embodiments, W is an unsubstituted heteroaryl ring. In some embodiments, W is pyridinyl. In some embodiments, W is S, $C_1$-$C_6$ alkyl, phenyl, or pyridinyl.

In some embodiments, b is 0. In some embodiments, b is 1.

In some embodiments, the compound is of Formula V wherein:
$R^{18}$ is unsubstituted $C_1$-$C_6$ alkyl or —C(O)CH$_3$;
$R^{19}$ is H, —NHCH$_3$, —N(CH$_3$)$_2$, or 1,2,4-triazolyl optionally substituted with $C_1$-$C_6$ alkyl;
Q is —SO$_2$— or —C(O)—;
W is S, unsubstituted $C_1$-$C_6$ alkyl, phenyl, or pyridinyl; and
b is 0 or 1.

In some embodiments, the compound of Formula I, Formula II, Formula III, Formula IV, or Formula V or a stereoisomer, tautomer, or pharmaceutically acceptable salt thereof, is selected from the group consisting of -continued

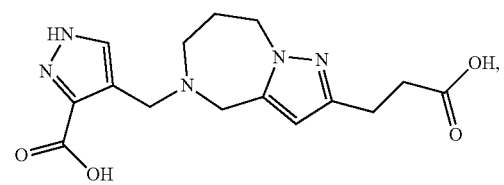

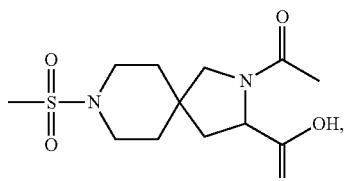

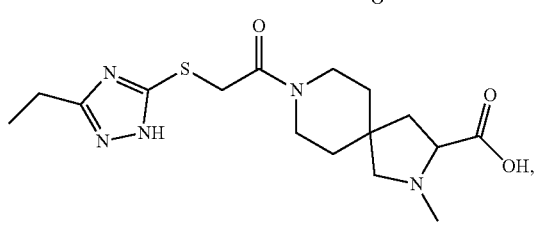

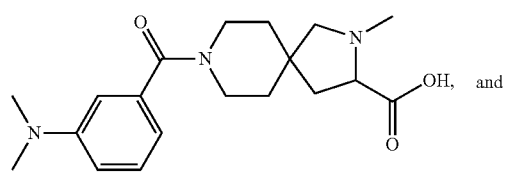

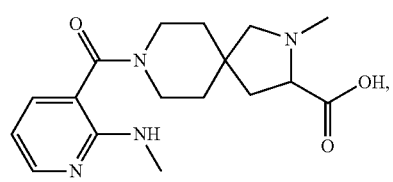

or a stereoisomer, tautomer, or pharmaceutically acceptable salt thereof.

In another aspect, disclosed herein is a compound selected from the group consisting of:

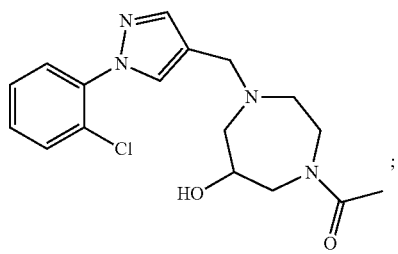

(1-acetyl-4-{[1-(2-chlorophenyl)-1H-pyrazol-4-yl]methyl}-1,4-diazepan-6-ol);

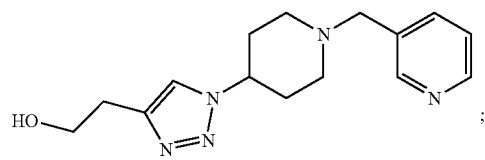

(2-{1-[1-(3-pyridinylmethyl)-4-piperidinyl]-1H-1,2,3-triazol-4-yl}ethanol)

-continued

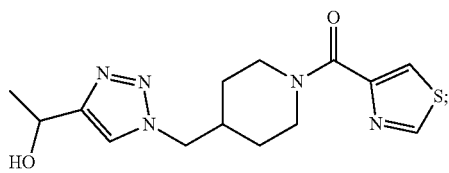

(1-(1-{[1-(1,3-thiazol-4-ylcarbonyl)-4-piperidinyl]methyl}-1H-1,2,3-triazol-4-yl)ethanol)

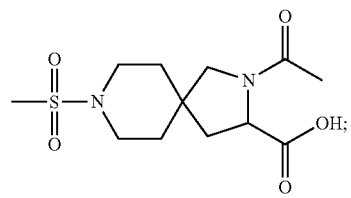

(2-acetyl-8-(methylsulfonyl)-2,8-diazaspiro[4.5]decane-3-carboxylic acid)

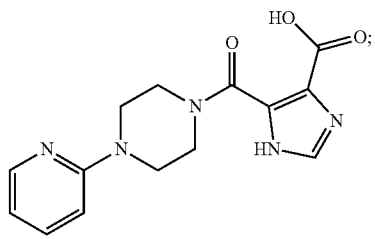

(5-[(4-pyridin-2-ylpiperazin-1-yl)carbonyl]-1H-imidazole-4-carboxylic acid)

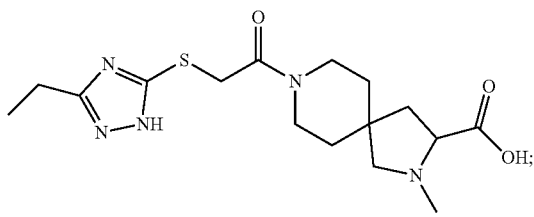

(8-{[(3-ethyl-1H-1,2,4-triazol-5-yl)thio]acetyl}-2-methyl-2,8-diazaspiro[4.5]decane-3-carboxylic acid)

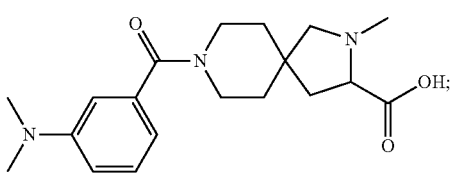

(8-[3-(dimethylamino)benzoyl]-2-methyl-2,8-diazaspiro[4.5]decane-3-carboxylic acid)

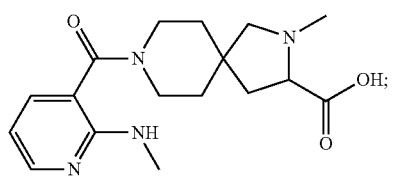

(2-methyl-8-{[2-(methylamino)-3-pyridinyl]carbonyl}-2,8-diazaspiro[4.5]decane-3-carboxylic acid);

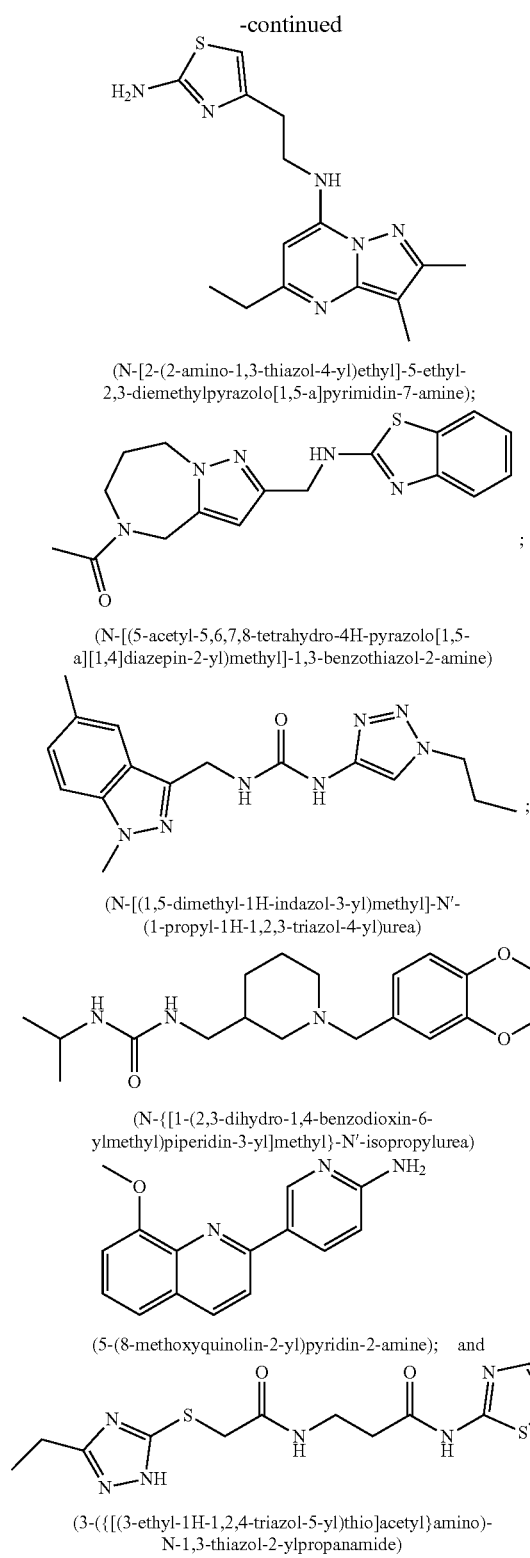

(N-[2-(2-amino-1,3-thiazol-4-yl)ethyl]-5-ethyl-
2,3-diemethylpyrazolo[1,5-a]pyrimidin-7-amine);

(N-[(5-acetyl-5,6,7,8-tetrahydro-4H-pyrazolo[1,5-
a][1,4]diazepin-2-yl)methyl]-1,3-benzothiazol-2-amine)

(N-[(1,5-dimethyl-1H-indazol-3-yl)methyl]-N'-
(1-propyl-1H-1,2,3-triazol-4-yl)urea)

(N-{[1-(2,3-dihydro-1,4-benzodioxin-6-
ylmethyl)piperidin-3-yl]methyl}-N'-isopropylurea)

(5-(8-methoxyquinolin-2-yl)pyridin-2-amine); and (3-({[(3-ethyl-1H-1,2,4-triazol-5-yl)thio]acetyl}amino)-
N-1,3-thiazol-2-ylpropanamide)

or a stereoisomer, tautomer, or pharmaceutically acceptable salt thereof.

In another aspect, disclosed herein is a compound selected from Table 1, or a stereoisomer, tautomer, or pharmaceutically acceptable salt thereof.

The compounds disclosed herein may be purchased from commercial sources or prepared using methods known to one skilled in the art. Schemes 1-6 depict non-limiting strategies to obtain select compounds of Formulas I, II, III, IV, and V. Exemplary compounds shown in Table 1 are commercially available and purchased from Chembridge.

Select compounds of Formula I may be prepared according to Scheme 1 or Scheme 2. In Scheme 1, 3-(Boc-aminomethyl)piperidine undergoes reductive amination with an appropriate aldehyde prior to removal of the Boc-protecting group and subsequent coupling of the primary amine with, for example, an isocyanate or CDI/amine, to form the urea product. In Scheme 2, 1-Boc-3-(aminomethyl)piperidine is converted to a urea intermediate as described above prior to removing the Boc-protecting group. Reductive amination of the free amine then affords select compounds of Formula I.

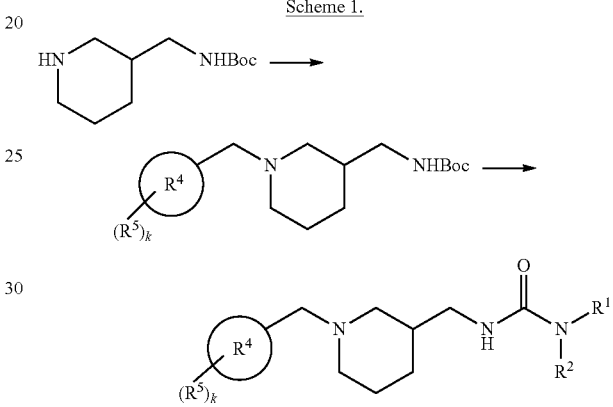

Scheme 1.

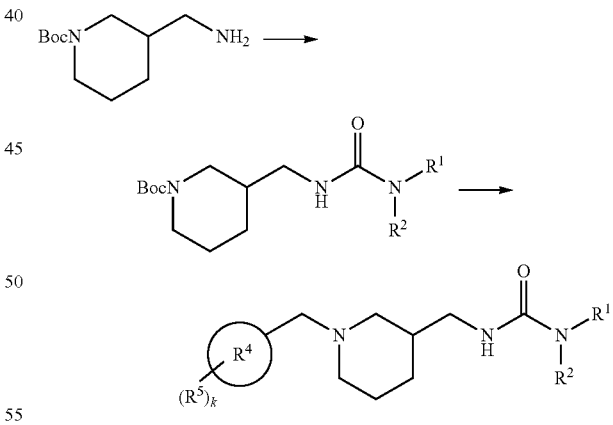

Scheme 2.

Select compounds of Formula II may be prepared according to Scheme 3. A 2-bromoquinoline undergoes a Suzuki reaction with an appropriate aryl boronic acid/boronate ester or heteroaryl boronic acid/boronate ester to afford select compounds of Formula II. Alternatively, the 2-bromoquinoline may be converted to a boronic acid or boronate ester for Suzuki reaction with an appropriate aryl halide or heteroaryl halide or other analogous Suzuki coupling partner.

Scheme 3.

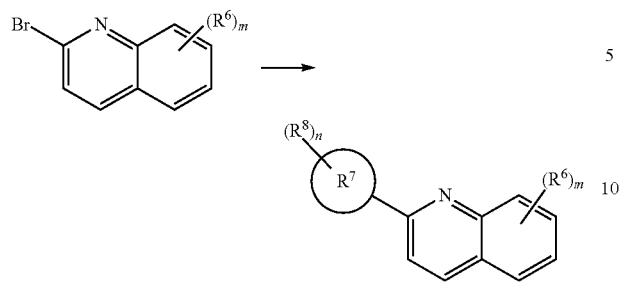

Select compounds of Formula III may be prepared according to Scheme 4. The appropriate aminoalkanoic acid (PG=protecting group) is coupled with amine followed by removal of the protecting group. The free amine may then be coupled with chloroacetic acid. Nucleophilic displacement with the appropriate aryl or heteroaryl thiol or alcohol results in select compounds of Formula III.

Scheme 4.

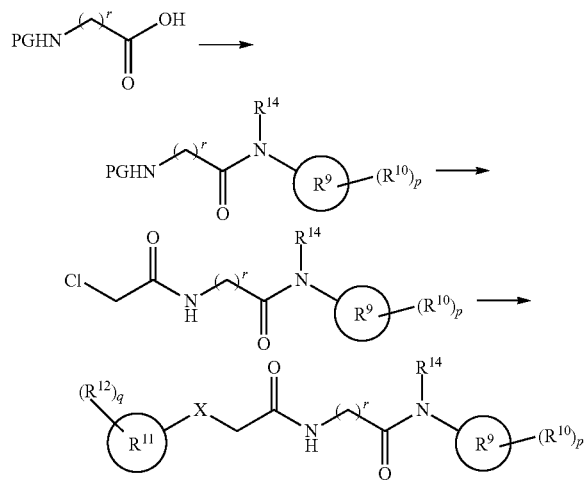

Select compounds of Formula IV may be prepared according to Scheme 5. The appropriate 5,6,7,8-tetrahydro-4H-pyrazolo[1,5-a][1,4]diazepine-2-carboxylic acid (PG=protecting group) undergoes a single carbon extension by reduction of the carboxylic acid, activation of the primary alcohol and subsequent nucleophilic displacement with nitrile, and hydrolysis of the nitrile intermediate into a carboxylic acid. The process may be optionally repeated until the desired alkyl chain length is obtained. Esterification followed by removal of the PG-protecting group is followed by reductive amination and saponification to arrive at certain compounds of Formula IV. Alternatively, any intermediate of the single carbon extension (e.g., primary alcohol or alkylnitrile) may be followed by removal of the PG-protecting group and reductive amination to arrive at other compounds of Formula IV. Moreover, the nucleophilic displacement of the activated primary alcohol may be performed with other nucleophiles (such as amines, alcohols, or thiols) prior to protecting group removal and reductive amination to arrive at yet other compounds of Formula IV.

Scheme 5.

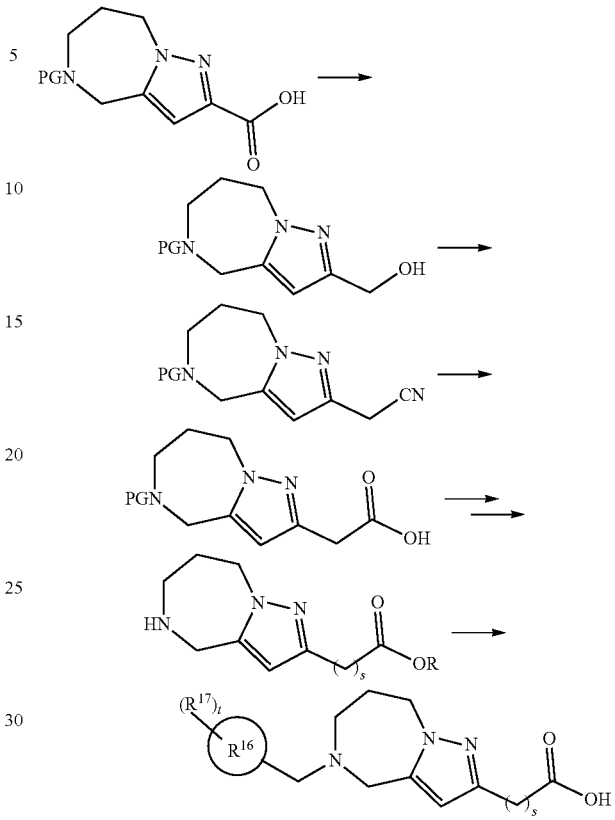

Select compounds of Formula V may be prepared according to Scheme 6. 2,8-Diazaspiro[4.5]decane-3,8-dicarboxylic acid 8-tert-butyl ester 3-ethyl ester undergoes acylation, sulfonylation, or reductive amination. The Boc-protecting group is then removed, and the free amine also undergoes acylation, sulfonylation, or reductive amination. Subsequent saponification provides certain compounds of Formula V.

Scheme 6.

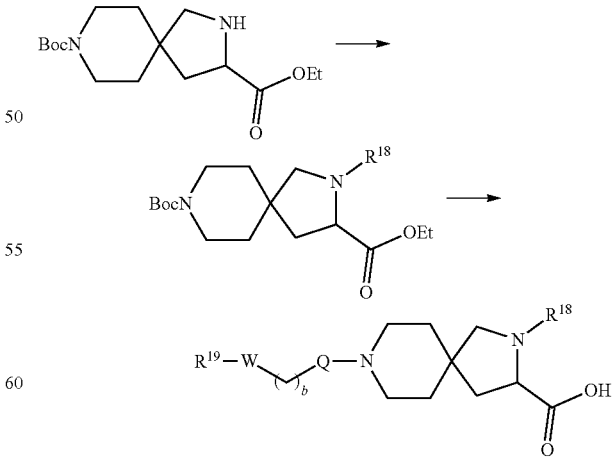

Salts, Solvates, Tautomers and Radioisotopes

Compounds of the present technology encompass all the salts of the compounds described herein. The present technology preferably includes all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, aspartinate, glutamate and the like.

Acid addition salts can be formed by mixing a solution of the particular compound described herein with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present technology with a solution of a pharmaceutically acceptable non-toxic base such as sodium hydroxide, potassium hydroxide, choline hydroxide, sodium carbonate and the like.

Compounds described herein also encompass solvates of any of the disclosed compounds. Solvates typically do not significantly alter the physiological activity or toxicity of the compounds, and as such may function as pharmacological equivalents. The term "solvate" as used herein is a combination, physical association and/or solvation of a compound described herein with a solvent molecule such as, e.g., a disolvate, monosolvate or hemisolvate, where the ratio of solvent molecule to compound described herein is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds described herein may be present as solvated forms with a pharmaceutically acceptable solvent, such as water, methanol, ethanol, and the like, and it is intended that the present technology includes both solvated and unsolvated forms of compounds described herein. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., J. Pharmaceut. Sci., 93(3):601-611 (2004), which describes the preparation of solvates of fluconazole with ethyl acetate and with water. Similar preparation of solvates, hemisolvates, hydrates, and the like are described by E. C. van Tonder et al., AAPS Pharm. Sci. Tech., 5(1) Article 12 (2004), and A. L. Bingham et al, Chem. Commun.: 603-604 (2001). A typical, non-limiting, process of preparing a solvate would involve dissolving a compound described herein in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the present technology also encompass tautomers of any of the disclosed compounds described herein.

Compounds of the present technology can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^5N$, $^{18}O$, $^{17}O$, $^{31}P$, $^{32}P$, $^{35}S$, $^{18}F$ and $^{36}Cl$, respectively, and preferably $^3H$, $^{13}C$, and $^{14}C$. Isotopically-labeled compounds of the present technology can be prepared by methods known in the art in view of this disclosure. For example, tritiated compounds of the present technology can be prepared by introducing tritium into the particular compound by catalytic dehalogenation with tritium. This method may include reacting a suitable halogen-substituted precursor of a compound of the present technology with tritium gas in the presence of an appropriate catalyst such as Pd/C in the presence of a base. Other suitable methods for preparing tritiated compounds can be found in Filer, Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

Compositions/Pharmaceutical Dosage Forms

When administered to a patient, a compound described herein can be administered as a component of a composition that comprises one or more pharmaceutically acceptable carriers and/or excipients. A compound described herein can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a compound of the present technology into the bloodstream.

Pharmaceutical compositions described herein can take the form of solutions, suspensions, emulsions, tablets, pills, pellets, powders, multi-particulates, capsules, capsules containing liquids, capsules containing powders, capsules containing multiparticulates, lozenges, sustained-release formulations, suppositories, transdermal patches, transmucosal films, sublingual tablets or tabs, aerosols, sprays, or any other form suitable for use. In one embodiment, the composition is in the form of a tablet. In another embodiment, the composition is in the form of a capsule (see, e.g., U.S. Pat. No. 5,698,155). Other examples of suitable pharmaceutical excipients are described in Remington's Pharmaceutical Sciences 1447-1676 (Alfonso R. Gennaro ed., 19th ed. 1995), incorporated herein by reference.

Pharmaceutical compositions described herein preferably comprise a suitable amount of a pharmaceutically acceptable excipient so as to provide the form for proper administration to the patient. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Water is a particularly useful excipient when a compound of the present technology is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The present technology compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, American Pharmaceutical Association (1986).

In certain embodiments, the compounds described herein are formulated for oral administration. A compound described herein to be orally delivered can be in the form of tablets, capsules, gelcaps, caplets, lozenges, aqueous or oily solutions, suspensions, granules, powders, emulsions, syrups, or elixirs, for example. When a compound described herein is incorporated into oral tablets, such tablets can be compressed, tablet triturates, enteric-coated, sugar-coated, film-coated, multiply compressed or multiply layered.

An orally administered compound described herein can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in Pharmaceutical Dosage Forms: Tablets (Lieberman, Lachman and Schwartz, eds., 2nd ed.) published by Marcel Dekker, Inc. Techniques and compositions for making tablets (compressed and molded), capsules (hard and soft gelatin) and pills are also described in Remington's Pharmaceutical Sciences 1553-1593 (Arthur Osol, ed., 16th ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in Pharmaceutical Dosage Forms: Disperse Systems, (Lieberman, Rieger and Banker, eds.) published by Marcel Dekker, Inc.

When a compound described herein is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a compound described herein is to be injected parenterally, it can be, e.g., in the form of an isotonic sterile solution. A compound of the present technology can also be in the form of a powder for reconstitution as an injectable formulation.

In certain embodiments, a compound described herein can be delivered in an immediate release form. In other embodiments, a compound described herein can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a compound of the present technology to treat or prevent the condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the compound of the present technology, and can thus reduce the occurrence of adverse side effects.

Controlled- or sustained-release compositions can initially immediately release an amount of a compound of the present technology that promptly produces the desired therapeutic or prophylactic effect, and gradually and continually release other amounts of the compound of the present technology to maintain a level of therapeutic or prophylactic effect over an extended period of time. To maintain a constant level of the compound of the present technology in the body, the compound of the present technology can be released from the dosage form at a rate that will replace the amount of compound of the present technology being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds. Controlled-release and sustained-release means for use according to the present disclosure may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the present technology in view of this disclosure. See also Goodson, "Dental Applications" (pp. 1 15-138) in Medical Applications of Controlled Release, Vol. 2, Applications and Evaluation, R. S. Langer and D. L. Wise eds., CRC Press (1984). Other controlled- or sustained-release systems that are discussed in the review by Langer, Science 249: 1527-1533 (1990) can be selected for use according to the present technology. In one embodiment, a pump can be used (Langer, Science 249: 1527-1533 (1990); Sefton, CRC Crit. Re Biomed. Eng. 74:201 (1987); Buchwald et al, Surgery 88:507 (1980); and Saudek et al., N. Engl. J. Med. 321:574 (1989)). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, J. Macromol. Sci. Rev. Macromol. Chem. 25:61 (1983); Levy et al., Science 225: 190 (1985); During et al., Ann. Neurol. 25:351 (1989); and Howard et al., J. Neurosurg. 7i:105 (1989)). In yet another embodiment, a controlled- or sustained-release system can be placed in proximity of a target of a compound of the present technology, e.g., the spinal column, brain, or gastrointestinal tract, thus requiring only a fraction of the systemic dose.

When in tablet or pill form, a pharmaceutical composition described herein can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions described herein include single unit dosage forms suitable for oral administration such as, but not limited to, tablets, capsules, gelcaps, and caplets that are adapted for controlled- or sustained-release.

In some embodiments, the compounds disclosed herein are administered at less than about 1 gram per day. In some embodiments, the compounds disclosed herein are administered at less than about 10, at less than about 9, at less than about 8, at less than about 7, at less than about 6, at less than about 5, less than about 4, less than about 3, less than about 2, less than about 1, less than about 0.9, less than about 0.8, less than about 0.7, less than about 0.6, less than about 0.5, less than about 0.4, less than about 0.3, less than about 0.2, or less than about 0.1 grams per day, or any amount in between these values.

The compound disclosed herein may be administered to the subject in an amount that is effective for the method disclosed herein. For example, but not by way of limitation, the amount of compound disclosed herein administered may be from about 0.2 mg/kg to about 100 mg/kg. In some embodiments the compound disclosed herein is administered from about 1 mg/kg to about 50 mg/kg. In yet other embodiments, the compound disclosed herein is administered to the subject from about 10 mg/kg to about 50 mg/kg. In some embodiments, the compound disclosed herein is administered to the subject from about 0.2 mg/kg to about 75 mg/kg. In some embodiments, the compound disclosed herein is administered to the subject from about 0.2 mg/kg to about 50 mg/kg. In some embodiments, the compound disclosed herein is administered to the subject from about 0.2 mg/kg to about 25 mg/kg. In some embodiments, the compound disclosed herein is administered to the subject from about 0.2 mg/kg to about 10 mg/kg. In some embodiments, the compound disclosed herein is administered to the subject from about 0.2 mg/kg to about 5 mg/kg. In some embodiments, the compound disclosed herein is administered to the subject from about 1 mg/kg to about 40 mg/kg. In some embodiments, the compound disclosed herein is administered to the subject from about 1 mg/kg to about 30 mg/kg. In some embodiments, the compound disclosed herein is administered to the subject from about 1 mg/kg to about 20 mg/kg. In some embodiments, the compound disclosed herein is administered to the subject from about 1 mg/kg to about 10 mg/kg. In some embodiments, the compound disclosed herein is administered to the subject from about 10 mg/kg to about 40 mg/kg. In some embodiments, the compound disclosed herein is administered to the subject from about 10 mg/kg to about 30 mg/kg. In some embodiments, the compound disclosed herein is administered to the subject from about 10 mg/kg to about 20 mg/kg.

Methods

In one aspect, provided herein are methods to inhibit the growth of a cancer cell or to treat cancer in a subject in need thereof, the methods comprising, or alternatively consisting essentially of, or yet further consisting of, administering to the cell or subject a compound disclosed herein. In one aspect, an effective amount, e.g., a therapeutically effective amount is administered to the cell or subject. In one aspect, treatment excludes prevention. In some embodiments, the subject is a mammal. In some embodiments, the mammal is human. In some embodiments, the mammal is non-human. In some embodiments, the mammal is a mouse, rat, guinea pig, dog, cat, monkey, cow, or horse. In some embodiments, the cancer is from heart sarcoma, lung cancer, small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; cancer of the gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); cancer of the genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); cancer of the liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); cancer of bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; cancer of the nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiforme, oligodendroglioma, schwannoma, retinoblastoma, congenital tumors), spinal cord neurofibroma, meningioma, glioma, sarcoma); cancer of the reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; cancer of the hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; cancer of the oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; cancer of the skin, for example, malignant melanoma, cutaneous melanoma, basal cell carcinoma, squamous cell carcinoma, Karposi's sarcoma, moles dysplastic nevi, lipoma, angioma, dermatofibroma, and keloids; cancer of the adrenal glands: neuroblastoma; and cancer of other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites. When treating cancer, the therapy can be combined with other therapies, and/or can be administered as a first line, second line, third line, fourth line or fifth line therapy. The amount to be administered will be determined by the treating veterinarian or physician and will vary with the disease, the subject and any additional therapies to be administered. When administered in vitro, the compound can be used as a pre-clinical diagnostic to determine if the compound will treat a subject's cancer or inflammatory disease, alone or in combination with other therapies. It also can be administered to a laboratory animal as a pre-clinical animal model. In some embodiments, the cancer is lung cancer, breast cancer, pancreatic cancer, liver cancer, glioblastoma, or melanoma.

In another aspect, provided herein are methods to treat inflammatory disease in a subject in need thereof, the methods comprising, or alternatively consisting essentially of, or yet further consisting of, administering to the subject a compound disclosed herein. In some embodiments, the subject is a mammal. In some embodiments, the mammal is human. In some embodiments, the mammal is non-human. In one aspect, an effective amount is administered. The amount to be administered will be determined by the treating veterinarian or physician and will vary with the disease, the subject and any additional therapies to be administered. When administered in vitro, the compound can be used as a pre-clinical diagnostic to determine if the compound will treat a subject's inflammatory disease, alone or in combination with other therapies. It also can be administered to a laboratory animal as a pre-clinical animal model.

As used herein, exemplary inflammatory diseases include, but are not limited to, multiple sclerosis, neuroinflammatory disease, muscle injuries, radiation tissue damage, stroke, traumatic brain injury, myocardial infarction, graft versus host disease, Parkinson's disease, Alzheimer's disease, inflammatory bowel disease, Huntington's disease, amyotrophic lateral sclerosis, Behcet's disease, COPD, NASH, sarcopenia, aging, spinal cord injury, wound repair, and dysphagia. Additional inflammatory diseases include autoimmune disease or disorders.

As used herein, "neuroinflammatory disease" or "neuroinflammation" is inflammation of the nervous tissue and related diseases or conditions. In some embodiments, neuroinflammation is an immune response that causes damage to the central nervous system. Neuroinflammation can be caused by infection, traumatic brain injury, toxic metabolites, neurodegeneration, and/or autoimmunity. Exemplary neuroinflammatory diseases include but are not limited to acute disseminated encephalomyelitis (ADEM), Optic Neuritis (ON), Transverse Myelitis, Neuromyelitis Optica (NMO), Alzheimer's disease, Parkinson's disease, multiple sclerosis, and traumatic brain injury.

As used herein, "autoimmune disease or disorder" includes diseases or disorders arising from and directed against an individual's own tissues or organs or manifestation thereof or a condition resulting there from. In some embodiments, it refers to a condition that results from, or is aggravated by, the production by T cells that are reactive with normal body tissues and antigens. Examples of autoimmune diseases or disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica spectrum disorder (NMO, also known as Devic's Disease or Devic's Syndrome), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, erythema multiforme, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, Type I diabetes, Type II diabetes, latent autoimmune diabetes in adults (or Type 1.5 diabetes) Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatic, giant cell arteritis and Takayasu's arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, anti-phospholipid syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, acquired thrombocytopenic purpura, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Graves disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, coronavirus infection, sepsis associated with MRSA and other bacterial infections, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, polyradiculitis acuta, Quervain's thyreoiditis, acquired spenic atrophy, nonmalignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, multiple organ injury syndrome, antiglomerular basement membrane disease, oophoritis, primary myxedema, autoimmune atrophic gastritis, sympathetic ophthalmia, rheumatic diseases, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, emphysema, alopecia areata, adipose tissue inflammation/diabetes type II, obesity associated adipose tissue inflammation/insulin resistance, and endometriosis.

In another aspect, provided herein are methods to stimulate M1 macrophage polarization, the methods comprising, or consisting essentially of, or yet further consisting of contacting a macrophage with a compound disclosed herein. In some embodiments, the contacting of the macrophage is performed in an in vitro assay. In some embodiments, the contacting of the macrophage is performed in an in vivo assay. In one aspect, an effective amount or a therapeutically effective amount is administered. The compound can be combined with other therapies. The amount to be administered will be determined by the treating veterinarian or physician and will vary with the disease, the subject and any additional therapies to be administered. When administered in vitro, the compound can be used as a pre-clinical diagnostic to determine if the compound will treat a subject's disease alone or in combination with other therapies. It also can be administered to a laboratory animal as a pre-clinical animal model. In one aspect, treatment excludes prevention.

In another aspect, provided herein are methods to inhibit M2 macrophage polarization, the methods comprising, or alternatively consisting essentially of, or yet further consisting of, contacting a macrophage with a compound disclosed herein. In some embodiments, the contacting of the macrophage is performed in an in vitro assay. In some embodiments, the contacting of the macrophage is performed in an in vivo assay. In one aspect, an effective amount or a therapeutically effective amount of the compound is contacted. The compound can be combined with other therapies. The amount to be contacted will be determined by the treating veterinarian or physician and will vary with the disease, the subject and any additional compounds or therapies are to be contacted. When administered in vitro, the compound can be used as a pre-clinical diagnostic to determine if the compound will treat a subject's disease alone or in combination with other therapies. It also can be administered to a laboratory animal as a pre-clinical animal model.

In another aspect, provided herein are methods to suppress macrophage-mediated immune suppression in a subject in need thereof, the methods comprising, or alternatively consisting essentially of, or yet further consisting of administering to the subject a compound disclosed herein. In one aspect, an effective amount or a therapeutically effective amount is administered. The compound can be combined with other therapies. The amount to be administered will be determined by the treating veterinarian or physician and will vary with the disease, the subject and any additional therapies to be administered. When administered in vitro, the compound can be used as a pre-clinical diagnostic to determine if the compound will treat a subject's disease alone or in combination with other therapies. It also can be administered to a laboratory animal as a pre-clinical animal model. In one aspect, treatment excludes prevention.

The present technology, thus generally described, will be understood more readily by reference to the following examples, which are provided by way of illustration and are not intended to be limiting of the present technology.

EXAMPLES

Example 1

Computational tools were used to analyze and model existing PI3K inhibitors in order to identify a unique binding pocket external to the ATP binding site. Commercially available chemical compound libraries were examined for binding to the unique binding site (allosteric binding site) and to the ATP binding site.

Primary and Secondary Screening:

Primary screening was performed on 507 compounds identified by the above-described computational screening. Bone marrow derived macrophages were plated into 96 well plates at d7 post-harvest and incubated with 1 µM compound and polarization reagents for 24 h. Primary screening was performed on cells polarized with interferon gamma (IFNg)+Lipopolysaccharide (LPS) (M1 polarization). Methods of inducing macrophage polarization are known in the art, e.g., as described in Mosser et al., Curr. Protoc. Immunol. 2008 November; Chapter 14:Unit 14.2. doi: 10.1002/0471142735.im1402s83. After 24 h, cell supernatants were removed and screened for IL12b and CCL2 protein levels using an enzyme linked immunosorbent assay (ELISA). Additionally, viability of polarized macrophages incubated with compounds was measured using an MTT assay, a colorimetric assay that measures cell metabolic activity by quantifying NAD(P)H-dependent cellular oxidoreductase reduction of the tetrazolium dye MTT 3-(4,5-dimethylthiazol-2-yl)-2,5-diphenyltetrazolium bromide to its insoluble purple colored formazan. Compounds that increased IL12b protein levels or decreased CCL2 protein levels and reduced viability less than 10% were selected for secondary screening. Secondary screening was performed as described for primary screening with a subset of 141 of the original compounds.

RNA Screening:

Compounds with the highest activity levels in the primary and secondary screening assays were tested for their effects on transcription of inflammatory cytokines after M1 (IFNg+ LPS) and M2 (IL-4) macrophage polarization. Bone marrow derived macrophages were plated into 12 well plates at d7 post-harvest and incubated for 1 h with 1 µM compound prior to polarization. Cell were then polarized by the addition of either IFNgamma+LPS (M1) or IL-4 (M2) and mRNA was harvested 6 h post-stimulation. Quantitative RT-PCR was used to determine the levels of IL-1beta expression in M1 polarized macrophages and of Arginase-1 and TGF-beta expression in M2 polarized macrophages. Compounds were selected from RNA screening that increased IL-1beta expression or decreased Arginase-1 or TGF-beta expression.

Select data is presented in Table 2 for compounds of Table 1.

TABLE 1

| Compd. No. | Chemical Structure Name | Structure |
|---|---|---|
| 1 | N-[(1,5-dimethyl-1H-indazol-3-yl)methyl]-N'-(1-propyl-1H-1,2,3-triazol-4-yl)urea | 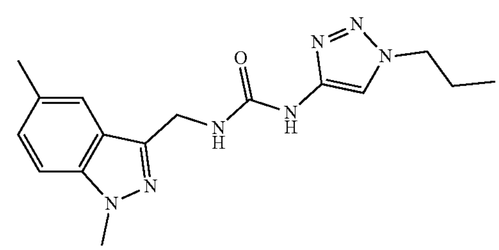 [SMILES: CCCn1cc(NC(=O)NCc2nn(C)c3ccc(C)cc23)nn1] |
| 2 | 5-(8-methoxyquinolin-2-yl)pyridin-2-amine | 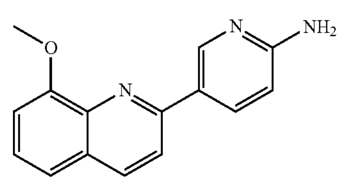 [SMILES: COc1cccc2ccc(-c3ccc(N)nc3)nc12] |
| 3 | 3-({[(3-ethyl-1H-1,2,4-triazol-5-yl)thio]acetyl}amino)-N-1,3-thiazol-2-ylpropanamide | 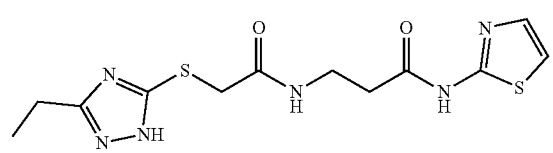 [SMILES: CCc1n[nH]c(SCC(=O)NCCC(=O)Nc2nccs2)n1] |

TABLE 1-continued

| Compd. No. | Chemical Structure Name | Structure |
|---|---|---|
| 4 | N-[2-(2-amino-1,3-thiazol-4-yl)ethyl]-5-ethyl-2,3-dimethylpyrazolo[1,5-a]pyrimidin-7-amine | 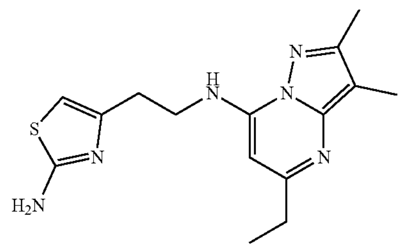 [SMILES: CCc1cc(NCCc2csc(N)n2)n2nc(C)c(C)c2n1] |
| 5 | N-[(5-acetyl-5,6,7,8-tetrahydro-4H-pyrazolo[1,5-a][1,4]diazepin-2-yl)methyl]-1,3-benzothiazol-2-amine | 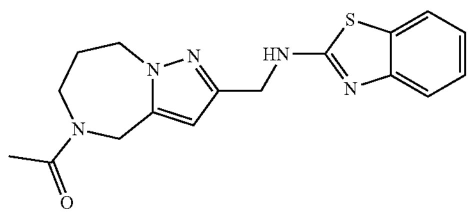 [SMILES: CC(=O)N1CCCn2nc(CNc3nc4ccccc4s3)cc2C1] |
| 6 | N-{[1-(2,3-dihydro-1,4-benzodioxin-6-ylmethyl)piperidin-3-yl]methyl}-N'-isopropylurea | 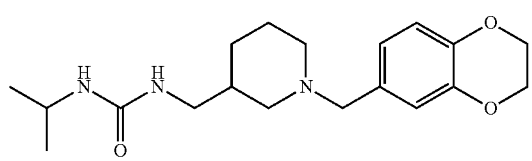 [SMILES: CC(C)NC(=O)NCC1CCCN(Cc2ccc3c(c2)OCCO3)C1] |
| 7 | 1-(1-{[1-(1,3-thiazol-4-ylcarbonyl)-4-piperidinyl]methyl}-1H-1,2,3-triazol-4-yl)ethanol | 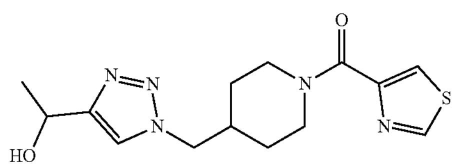 [SMILES: CC(O)c1cn(CC2CCN(C(=O)c3cscn3)CC2)nn1] |
| 8 | 2-acetyl-8-(methylsulfonyl)-2,8-diazaspiro[4.5]decane-3-carboxylic acid | 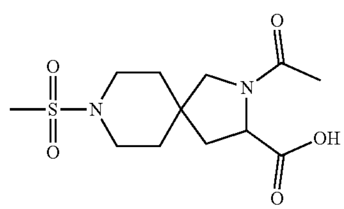 [SMILES: CC(=O)N1CC2(CCN(S(C)(=O)=O)CC2)CC1C(=O)O] |
| 9 | 5-[(4-pyridin-2-ylpiperazin-1-yl)carbonyl]-1H-imidazole-4-carboxylic acid | 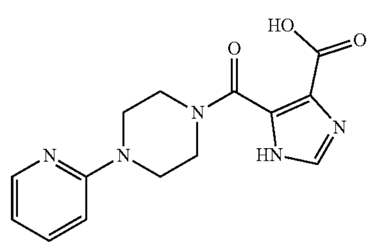 [SMILES: O=C(O)c1nc[nH]c1C(=O)N1CCN(c2ccccn2)CC1] |
| 10 | 1-acetyl-4-{[1-(2-chlorophenyl)-1H-pyrazol-4-yl]methyl}-1,4-diazepan-6-ol | 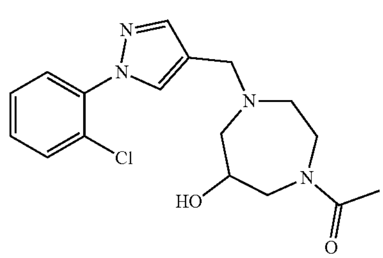 [SMILES: CC(=O)N1CCN(Cc2cnn(-c3ccccc3Cl)c2)CC(O)C1] |

TABLE 1-continued

| Compd. No. | Chemical Structure Name | Structure |
|---|---|---|
| 11 | 2-{1-[1-(3-pyridinylmethyl)-4-piperidinyl]-1H-1,2,3-triazol-4-yl}ethanol | 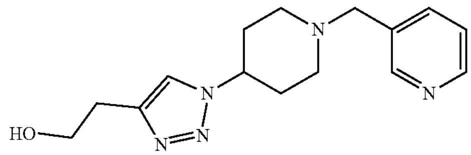 [SMILES: OCCc1cn(C2CCN(Cc3cccnc3)CC2)nn1] |
| 12 | 8-{[(3-ethyl-1H-1,2,4-triazol-5-yl)thio]acetyl}-2-methyl-2,8-diazaspiro[4.5]decane-3-carboxylic acid | 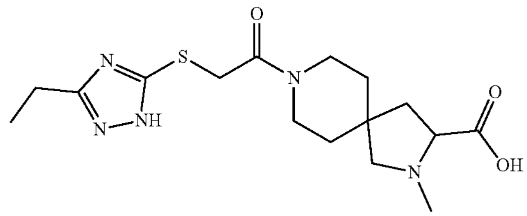 [SMILES: CCc1n[nH]c(SCC(=O)N2CCC3(CC2)CC(C(=O)O)N(C)C3)n1] |
| 13 | 8-[3-(dimethylamino)benzoyl]-2-methyl-2,8-diazaspiro[4.5]decane-3-carboxylic acid | 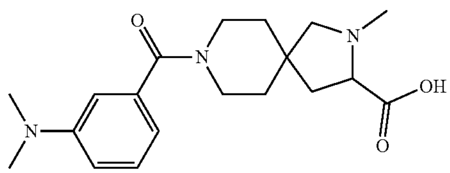 [SMILES: CN(C)c1cccc(C(=O)N2CCC3(CC2)CC(C(=O)O)N(C)C3)c1] |
| 14 | 2-methyl-8-{[2-(methylamino)-3-pyridinyl]carbonyl}-2,8-diazaspiro[4.5]decane-3-carboxylic acid | 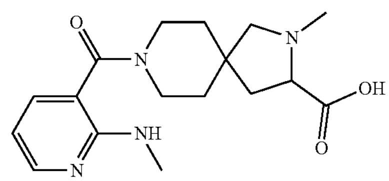 [SMILES: CNc1ncccc1C(=O)N1CCC2(CC1)CC(C(=O)O)N(C)C2] |
| 15 | 1-(4-(benzo[d][1,3]dioxol-5-yl)-3-hydroxypiperidin-1-yl)propan-1-one | 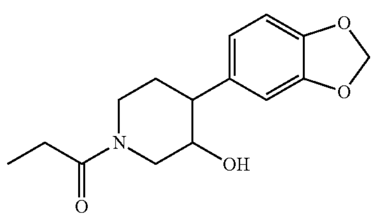 [SMILES: CCC(=O)N1CCC(c2ccc3c(c2)OCO3)C(O)C1] |
| 16 | 4-((2-(2-carboxyethyl)-7,8-dihydro-4H-pyrazolo[1,5-a][1,4]diazepin-5(6H)-yl)methyl)-1H-pyrazole-3-carboxylic acid | 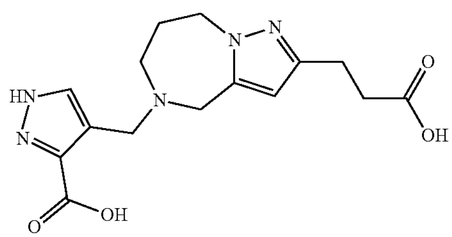 [SMILES: O=C(O)CCc1cc2n(n1)CCCN(Cc1c[nH]nc1C(=O)O)C2] |

TABLE 2

| | Primary Screen | | Secondary Screen | | RNA Screening | | |
|---|---|---|---|---|---|---|---|
| | | | | | IL-4 | | Ifng + LPS |
| Compd. No. | $Z_{IL12b}$ | $Z_{CCL2}$ | $Z_{IL12b}$ | $Z_{CCL2}$ | Arg 1 | Tgfb | Il1b |
| 1 | 0.93 | −1.85 | 1.05 | −0.72 | NA | NA | NA |
| 2 | | | 0.81 | 0.8 | − | − | + |
| 3 | | | 1.56 | 1.33 | − | = | = |
| 4 | 1.46 | 1.08 | 0.58 | −1.61 | NA | NA | NA |
| 5 | 1.64 | 1.04 | 0.72 | −1.33 | NA | NA | NA |
| 6 | 1.96 | 0.94 | 2.4 | 0.16 | − | − | + |
| 7 | 0.38 | −1.62 | 1.58 | −1.5 | -- | -- | + |
| 8 | 0.13 | −3.6 | 0.74 | −1.79 | NA | NA | NA |
| 9 | 0.54 | −5.07 | 0.92 | −1.53 | − | + | + |
| 10 | 0.55 | −1.59 | 1.64 | −0.36 | -- | -- | = |
| 11 | −1.17 | −2.99 | 2.04 | −1.46 | -- | − | + |
| 15 | | | 0.25 | −0.95 | -- | NA | + |
| 16 | | | 0.56 | −0.84 | -- | NA | + |

The Z score is equal to the measured value of the sample minus the mean of measured values of all samples divided by the standard deviation of the measured value. With regard to the RNA screening data: "−": significant decrease in mRNA vs control (mRNA levels above 50% of control); "−−": significant decrease in mRNA vs control (mRNA levels below 50% of control); "+": significant increase in mRNA vs control; "=": no significant change vs control; "N/A": not applicable (not tested).

Example 2: Testing of Selected PI3Kgamma Allosteric and Orthosteric Inhibitor Activity Compounds with the highest activity levels in the primary, secondary and tertiary screening assays were resynthesized in bulk and then tested for their effects on protein expression of inflammatory cytokines after M1 (IFNg+LPS) macrophage polarization. Bone marrow derived macrophages were plated into 12 well plates at d7 post-harvest and incubated for 1 h with 10 micromolar compound prior to polarization in the presence of bulk synthesized compounds 1-14. Cells were then polarized by the addition of either IFNgamma+LPS (M1) and cell supernatants were harvested 24 h post-stimulation. Methods of inducing macrophage polarization are known in the art, e.g., as described in Mosser et al., Curr. Protoc. Immunol. 2008 November; Chapter 14:Unit 14.2. doi: 10.1002/0471142735.im1402s83. After 24 h, cell supernatants were removed and screened for IL12b protein levels using an enzyme linked immunosorbent assay (ELISA). Increases in IL12b protein levels induced by compounds were recorded as percent increase in IL12b protein expression compared to IL12b expression in the absence of compounds. Results are shown in Table 3.

TABLE 3

| Compd. No. | Inhibitor Type* | MW | 10 mM stock (µL) | IL12B protein expression (Percent of Control) | Standard error IL12B protein expression (Percent of Control) |
| --- | --- | --- | --- | --- | --- |
| 1 | A | 327 | 305.8 | 134 | 4.5 |
| 2 | A | — | — | — | — |
| 3 | A | — | — | — | — |
| 4 | A | 316 | 316.5 | 92 | 3 |
| 5 | A | 341 | 293.3 | 127 | 3.5 |
| 6 | A | 347 | 288.2 | 120 | 3.3 |
| 7 | B | 321 | 311.5 | 114 | 2.2 |
| 8 | B | 304 | 328.9 | 118 | 4.5 |
| 9 | B | 301 | 332.2 | 131 | 4.6 |
| 10 | B | 349 | 386.5 | 121 | 1.9 |
| 11 | B | 287 | 348.4 | 127 | 2.8 |
| 12 | B | 367 | 272.5 | 133 | 5 |
| 13 | B | 345 | 289.9 | 125 | 2.5 |
| 14 | B | 332 | 301.2 | 122 | 3 |
| 15 | B | — | — | — | — |
| 16 | B | — | — | — | — |

*A = active site inhibitor; B = allosteric inhibitor

Example 3: Xenograft Mouse Model Studies

The impact of compounds disclosed herein in a mouse xenograft model is examined. In this model, cancer cells (e.g., lymphoma, leukemia, lung cancer, breast cancer, pancreatic cancer, liver cancer, glioblastoma, or melanoma) in PBS are injected into the Balb/C mice mammary fat pad. When tumors are palpable, tumor growth is measured for 3 weeks and calculated as 0.52×L×W×W (L=Length, W=Width). Ten days after cell injection, a solution of a compound disclosed herein or placebo is administered twice per week to the mice. The mice are sacrificed at the end of treatment, and the xenograft tumor is collected, formalin fixed, paraffin embedded, sectioned. Plasma samples are obtained from the animals at various time points post-dosing for the purpose of pharmacokinetic (PK) and pharmacodynamic (PD) analyses.

Example 4: Clinical Trial for Cancer

Cancer (e.g., lymphoma, leukemia, lung cancer, breast cancer, pancreatic cancer, liver cancer, glioblastoma, or melanoma) in adult subjects is confirmed histologically or cytologically prior to participation in the study. The adult subjects receive a compound disclosed herein. Subjects are monitored for reduction in tumor value.

Example 5: Clinical Trial for Acute Respiratory Distress Syndrome (ARDS)

Adult subjects with ARDS are treated with standard intensive care with or without a compound disclosed herein. Primary outcome measures include all-cause mortality at 60 days after enrollment in study. Secondary outcome measures include number of ventilator-free days (VFDs) at Day 28 (defined as days being alive and free from mechanical ventilation at day 28 after enrollment). For patients ventilated 28 days or longer and for subjects who die, VFD is 0. ARDS may be associated with coronavirus infection or other viral infections.

Example 6: Clinical Trial for COPD

Adult subjects with moderate to severe COPD are treated with a compound disclosed herein or placebo for four weeks. Primary outcome measures include spirometry assessments to assess pulmonary function including the forced expiratory volume in 1 second (FEV1). Peak FEV1 at Week 4 is defined as the maximum post-dose value among the 30 minutes, 1, 2 and 3 hour assessments collected at Visit 6. Baseline is defined as the FEV1 pre-dose assessment (−15 minutes) collected at Visit 2. A mixed model for repeated measures (MMRM) is used to model the change from baseline FEV1 using baseline FEV1 as a continuous fixed effect, randomized treatment, week and treatment-by-week as categorical fixed effect, and patient as random effect.

Secondary outcome measures include assessment of mean change from baseline FEV1 to morning trough FEV1 at Week 4 (time frame: baseline (pre-dose, Visit 2) and Week 4 (Visit 6)); and assessment of mean change from baseline FEV1 to average FEV1 (over 12 Hours) at Day 1 and Week 4 (time frame: baseline (pre-dose, Visit 2), up to 12 hours post-dose at Visit 2 (Day 1) and Visit 6 (Week 4)).

Example 7: Clinical Trial for NASH

Adult subjects with NASH are treated with a compound disclosed herein or placebo for 12 weeks. Primary outcome measures include change from baseline in alanine aminotransferase (ALT) levels. Secondary outcome measures include change from baseline in percentage of liver fat as measured by MRI, change from baseline in fasting lipid profile (HDL and LDL cholesterol), and change in baseline in fibrosis biomarker test.

Example 8: Clinical Trial for Crohn's Disease

Adult subjects with Crohn's disease are treated with a compound disclosed herein or placebo for 14 weeks. Primary outcome measures include proportion of subjects who achieve a 100-point decrease from baseline in Crohn's Disease Activity Index (CDAI) score at Visit 6 (Week 12).

Example 9: Clinical Trial for Multiple Sclerosis

Adult subjects with multiple sclerosis are treated with a compound disclosed herein or placebo for 6 months. Primary outcome measures include measurement of B-cell depletion.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member and is inclusive of the endpoints.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Para. A. A method to treat cancer or inflammatory disease in a subject in need thereof, the method comprising administering to the subject a therapeutically effective amount of a compound of Formula I, Formula II, Formula III, Formula IV, or Formula V, or a stereoisomer, tautomer, or pharmaceutically acceptable salt thereof:

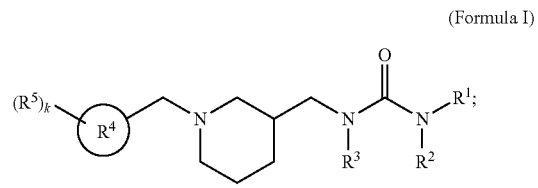

(Formula I)

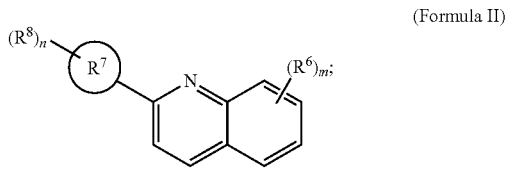

(Formula II)

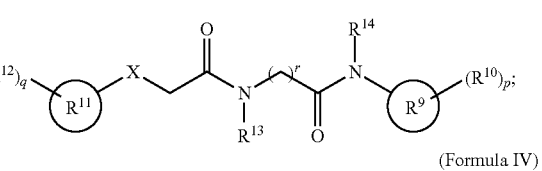

(Formula III)

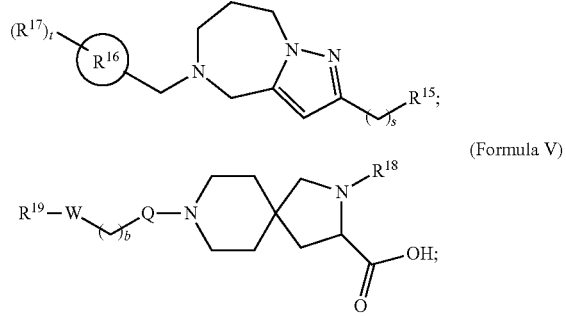

(Formula IV)

(Formula V)

wherein
$R^1$ is H or substituted or unsubstituted alkyl; $R^2$ is H or substituted or unsubstituted alkyl;
$R^3$ is H or substituted or unsubstituted alkyl; $R^4$ is aryl or heteroaryl;
each $R^5$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring; or two adjacent $R^5$, together with the atoms to which they are attached, form a substituted or unsubstituted cycloalkyl ring, a substituted or unsubstituted heterocyclyl ring, a substituted or unsubstituted aryl ring, or a substituted or unsubstituted heteroaryl ring;

each $R^6$ is independently selected from the group consisting of substituted or unsubstituted alkyl, halide, —CN, —NO$_2$, —SR''', —OR''', —NR'''R'', —C(O)R''', —C(O)OR''', —C(O)NR'''R'', —S(O)$_j$R''', —S(O)$_j$NR'''R'', —NR''C(O)R''', —NR''C(O)OR''', —NR''C(O)NR'''R$^p$, —NR''S(O)$_j$R''', —NR''S(O)$_j$NR'''R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^7$ is aryl or heteroaryl;

each $R^8$ is independently selected from the group consisting of substituted or unsubstituted alkyl, halide, —CN, —NO$_2$, —SR''', —OR''', —NR'''R'', —C(O)R''', —C(O)OR''', —C(O)NR'''R'', —S(O)$_j$R''', —S(O)$_j$NR'''R'', —NR''C(O)R''', —NR''C(O)OR''', —NR''C(O)NR'''R$^p$, —NR''S(O)$_j$R''', —NR''S(O)$_j$NR'''R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^9$ is aryl or heteroaryl;

each $R^{10}$ is independently selected from the group consisting of substituted or unsubstituted alkyl, halide, —CN, —NO$_2$, —SR''', —OR''', —NR'''R'', —C(O)R''', —C(O)OR''', —C(O)NR'''R'', —S(O)$_j$R''', —S(O)$_j$NR'''R'', —NR''C(O)R''', —NR''C(O)OR''', —NR''C(O)NR'''R$^p$, —NR''S(O)$_j$R''', —NR''S(O)$_j$NR'''R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{11}$ is aryl or heteroaryl;

each $R^{12}$ is independently selected from the group consisting of substituted or unsubstituted alkyl, halide, —CN, —NO$_2$, —SR''', —OR''', —NR'''R'', —C(O)R''', —C(O)OR''', —C(O)NR'''R'', —S(O)$_j$R''', —S(O)$_j$NR'''R'', —NR''C(O)R''', —NR''C(O)OR''', —NR''C(O)NR'''R$^p$, —NR''S(O)$_j$R''', —NR''S(O)$_j$NR'''R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{13}$ is H or substituted or unsubstituted alkyl; $R^{14}$ is H or substituted or unsubstituted alkyl;

$R^{15}$ is H, substituted or unsubstituted alkyl, halide, —CN, —NO$_2$, —SR''', —OR''', —NR'''R'', —C(O)R''', —C(O)OR''', —C(O)NR'''R'', —S(O)$_j$R''', —S(O)$_j$NR'''R'', —NR''C(O)R''', —NR''C(O)OR''', —NR''C(O)NR'''R$^p$, —NR''S(O)$_j$R''', —NR''S(O)$_j$NR'''R$^p$, a substituted or unsubstituted cycloalkyl ring, a substituted or unsubstituted heterocyclyl ring, a substituted or unsubstituted aryl ring, or a substituted or unsubstituted heteroaryl ring;

$R^{16}$ is aryl or heteroaryl;

each $R^{17}$ is independently selected from the group consisting of substituted or unsubstituted alkyl, halide, —CN, —NO$_2$, —SR''', —OR''', —NR'''R'', —C(O)R''', —C(O)OR''', —C(O)NR'''R'', —S(O)$_j$R''', —S(O)$_j$NR'''R'', —NR''C(O)R''', —NR''C(O)OR''', —NR''C(O)NR'''R$^p$, —NR''S(O)$_j$R''', —NR''S(O)$_j$NR'''R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{18}$ is H, substituted or unsubstituted alkyl, —C(O)R''', —C(O)OR''', —C(O)NR'''R'', —S(O)$_j$R''', —S(O)$_j$NR'''R'', a substituted or unsubstituted cycloalkyl ring, a substituted or unsubstituted heterocyclyl ring, a substituted or unsubstituted aryl ring, or a substituted or unsubstituted heteroaryl ring;

$R^{19}$ is H, substituted or unsubstituted alkyl, halide, —CN, —NO$_2$, —SR''', —OR''', —NR'''R'', —C(O)R''', —C(O)OR''', —C(O)NR'''R'', —S(O)$_j$R''', —S(O)$_j$NR'''R'', —NR''C(O)R''', —NR''C(O)OR''', —NR''C(O)NR'''R$^p$, —NR''S(O)$_j$R''', —NR''S(O)$_j$NR'''R$^p$, a substituted or unsubstituted cycloalkyl ring, a substituted or unsubstituted heterocyclyl ring, a substituted or unsubstituted aryl ring, or a substituted or unsubstituted heteroaryl ring;

Q is —SO$_2$— or —C(O)—;

W is S, substituted or unsubstituted alkyl, a substituted or unsubstituted aryl ring, or a substituted or unsubstituted heteroaryl ring;

X is O or S;

each R''', R'', and R$^p$ is independently selected from the group consisting of H, substituted or unsubstituted alkyl, a substituted or unsubstituted cycloalkyl ring, a substituted or unsubstituted heterocyclyl ring, a substituted or unsubstituted aryl ring, and a substituted or unsubstituted heteroaryl ring b is 0 or 1; j is 1 or 2; k is 0, 1, 2, 3, 4 or 5; m is 0, 1, 2, 3, or 4; n is 0, 1, 2, 3, 4, or 5; p is 0, 1, 2, 3, 4, or 5; q is 0, 1, 2, 3, 4, or 5; r is 1, 2, 3, 4, or 5; s is 1, 2, 3, 4, or 5; and t is 1, 2, 3, 4, or 5.

Para. B. A method to stimulate M1 macrophage polarization, the method comprising contacting a macrophage with a compound of Formula I, Formula II, Formula III, Formula IV, or Formula V, or a stereoisomer, tautomer, or pharmaceutically acceptable salt thereof:

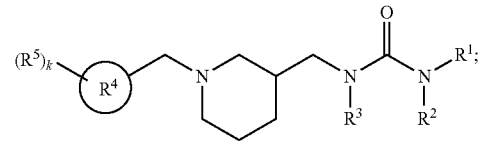

(Formula I)

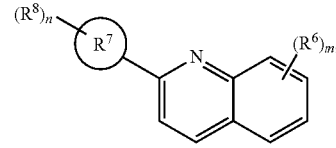

(Formula II)

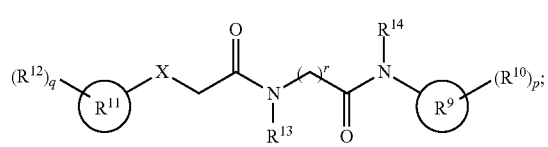

(Formula III)

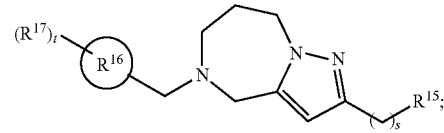

(Formula IV)

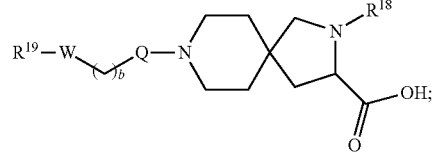

(Formula V)

wherein $R^1$ is H or substituted or unsubstituted alkyl; $R^2$ is H or substituted or unsubstituted alkyl;

$R^3$ is H or substituted or unsubstituted alkyl; $R^4$ is aryl or heteroaryl;

each $R^5$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring; or two adjacent $R^5$, together with the atoms to which they are attached, form a substituted or unsubstituted cycloalkyl ring, a substituted or unsubstituted heterocyclyl ring, a substituted or unsubstituted aryl ring, or a substituted or unsubstituted heteroaryl ring;

each $R^6$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^7$ is aryl or heteroaryl;

each $R^8$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^9$ is aryl or heteroaryl;

each $R^{10}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{11}$ is aryl or heteroaryl;

each $R^{12}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{13}$ is H or substituted or unsubstituted alkyl; $R^{14}$ is H or substituted or unsubstituted alkyl;

$R^{15}$ is H, substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, or a substituted or unsubstituted heteroaryl ring;

$R^{16}$ is aryl or heteroaryl;

each $R^{17}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;

$R^{18}$ is H, substituted or unsubstituted alkyl, —C(O)R$^m$, —C(O)OR$^m$, —C(O)NR$^m$R$^n$, —S(O)$_j$R$^m$, —S(O)$_j$NR$^m$R$^n$, a substituted or unsubstituted cycloalkyl ring, a substituted or unsubstituted heterocyclyl ring, a substituted or unsubstituted aryl ring, or a substituted or unsubstituted heteroaryl ring;

$R^{19}$ is H, substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, or a substituted or unsubstituted heteroaryl ring;

Q is —SO$_2$— or —C(O)—;

W is S, substituted or unsubstituted alkyl, a substituted or unsubstituted aryl ring, or a substituted or unsubstituted heteroaryl ring;

X is O or S;

each $R^m$, $R^n$, and $R^p$ is independently selected from the group consisting of H, substituted or unsubstituted alkyl, a substituted or unsubstituted cycloalkyl ring, a substituted or unsubstituted heterocyclyl ring, a substituted or unsubstituted aryl ring, and a substituted or unsubstituted heteroaryl ring;

b is 0 or 1; j is 1 or 2; k is 0, 1, 2, 3, 4 or 5; m is 0, 1, 2, 3, or 4; n is 0, 1, 2, 3, 4, or 5; p is 0, 1, 2, 3, 4, or 5; q is 0, 1, 2, 3, 4, or 5; r is 1, 2, 3, 4, or 5; s is 1, 2, 3, 4, or 5; and t is 1, 2, 3, 4, or 5.

Para. C. A method to inhibit M2 macrophage polarization, the method comprising contacting a macrophage with a compound of Formula I, Formula II, Formula III, Formula IV, or Formula V, or a stereoisomer, tautomer, or pharmaceutically acceptable salt thereof:

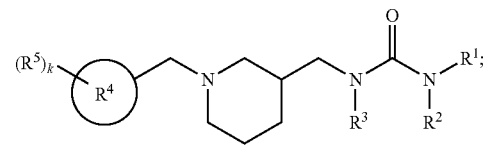

(Formula I)

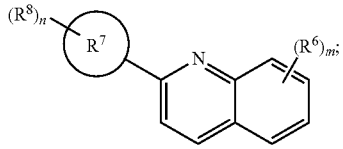

(Formula II)

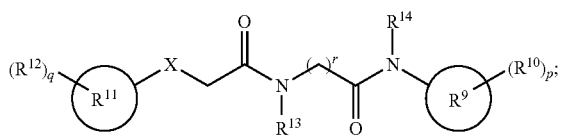

(Formula III)

-continued

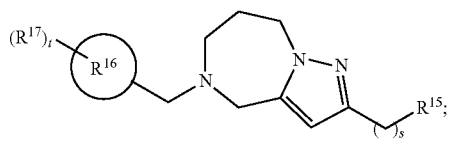

(Formula IV)

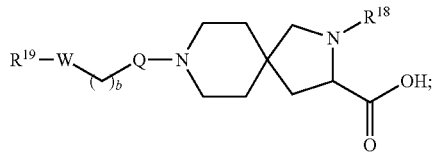

(Formula V)

wherein
R$^1$ is H or substituted or unsubstituted alkyl; R$^2$ is H or substituted or unsubstituted alkyl;
R$^3$ is H or substituted or unsubstituted alkyl; R$^4$ is aryl or heteroaryl;
each R$^5$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring; or two adjacent R$^5$, together with the atoms to which they are attached, form a substituted or unsubstituted cycloalkyl ring, a substituted or unsubstituted heterocyclyl ring, a substituted or unsubstituted aryl ring, or a substituted or unsubstituted heteroaryl ring;
each R$^6$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;
R$^7$ is aryl or heteroaryl;
each R$^8$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;
R$^9$ is aryl or heteroaryl;
each R$^{10}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;
R$^{11}$ is aryl or heteroaryl;
each R$^{12}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;
R$^{13}$ is H or substituted or unsubstituted alkyl; R$^{14}$ is H or substituted or unsubstituted alkyl;
R$^{15}$ is H, substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, or a substituted or unsubstituted heteroaryl ring;
R$^{16}$ is aryl or heteroaryl;
each R$^{17}$ is independently selected from the group consisting of substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, and a substituted or unsubstituted heteroaryl ring;
R$^{18}$ is H, substituted or unsubstituted alkyl, —C(O)R$^m$, —C(O)OR$^m$, —C(O)NR$^m$R$^n$, —S(O)$_j$R$^m$, —S(O)$_j$NR$^m$R$^n$, a substituted or unsubstituted cycloalkyl ring, a substituted or unsubstituted heterocyclyl ring, a substituted or unsubstituted aryl ring, or a substituted or unsubstituted heteroaryl ring;
R$^{19}$ is H, substituted or unsubstituted alkyl, halide, —CN, —NO$_2$, —SR$^m$, —OR$^m$, —NR$^m$R$^n$, —C(O)R$^m$, —C(O)OR$^m$, —C(O)NR$^m$R$^n$, —S(O)$_j$R$^m$, —S(O)$_j$NR$^m$R$^n$, —NR$^n$C(O)R$^m$, —NR$^n$C(O)OR$^m$, —NR$^n$C(O)NR$^m$R$^p$, —NR$^n$S(O)$_j$R$^m$, —NR$^n$S(O)$_j$NR$^m$R$^p$, a substituted or unsubstituted cycloalkyl ring, a substituted or unsubstituted heterocyclyl ring, a substituted or unsubstituted aryl ring, or a substituted or unsubstituted heteroaryl ring;
Q is —SO$_2$— or —C(O)—;
W is S, substituted or unsubstituted alkyl, a substituted or unsubstituted aryl ring, or a substituted or unsubstituted heteroaryl ring;
X is O or S;
each R$^m$, R$^n$, and R$^p$ is independently selected from the group consisting of H, substituted or unsubstituted alkyl, a substituted or unsubstituted cycloalkyl ring, a substituted or unsubstituted heterocyclyl ring, a substituted or unsubstituted aryl ring, and a substituted or unsubstituted heteroaryl ring;
b is 0 or 1; j is 1 or 2; k is 0, 1, 2, 3, 4 or 5; m is 0, 1, 2, 3, or 4; n is 0, 1, 2, 3, 4, or 5; p is 0, 1, 2, 3, 4, or 5; q is 0, 1, 2, 3, 4, or 5; r is 1, 2, 3, 4, or 5; s is 1, 2, 3, 4, or 5; and t is 1, 2, 3, 4, or 5.

Para. D. The method of Paras. B or C, wherein the contacting of the macrophage is performed in an in vitro assay.

Para. E. The method of Paras. B or C, wherein the contacting of the macrophage is performed in an in vivo assay.

Para. F. The method of any one of Paras. A-E, wherein the compound is of Formula I wherein R$^1$ is H or substituted or unsubstituted C$_1$-C$_6$ alkyl; R$^2$ is H or substituted or unsubstituted C$_1$-C$_6$ alkyl; R$^3$ is H or substituted or unsubstituted C$_1$-C$_6$ alkyl; R$^4$ is aryl; each R$^5$ is independently selected from the group consisting of substituted or unsubstituted $C_1$-$C_6$ alkyl, halide, —CN, —NO$_2$, —SR$'''$, —OR$'''$, and —NR$'''$R$''$, or two adjacent R$^5$, together with the atoms to which they are attached, form a substituted or unsubstituted 5- or 6-membered heterocyclyl ring; each R$'''$ and R$''$ is independently H or substituted or unsubstituted $C_1$-$C_6$ alkyl; and k is 0, 1, or 2.

Para. G. The method of Para. F, wherein R$^4$ is phenyl.

Para. H. The method of any one of Paras. A-E, wherein the compound is of Formula II wherein each R$^6$ is independently selected from the group consisting of substituted or unsubstituted $C_1$-$C_6$ alkyl, halide, —CN, —NO$_2$, —SR$'''$, —OR$'''$, and —NR$'''$R$''$; R$^7$ is heteroaryl; each R$^8$ is independently selected from the group consisting of substituted or unsubstituted $C_1$-$C_6$ alkyl, halide, —CN, —NO$_2$, —SR$'''$, —OR$'''$, and —NR$'''$R$''$; each R$'''$ and R$''$ is independently H or substituted or unsubstituted $C_1$-$C_6$ alkyl; m is 0, 1, or 2; and n is 0, 1, or 2.

Para. I. The method of Para. H, wherein R$^7$ is pyridinyl.

Para. J. The method of Para. H or Para. I, wherein n and m are both 1.

Para. K. The method of any one of Paras. A-E, wherein the compound is of Formula III wherein R$^9$ is heteroaryl; each R$^{10}$ is independently selected from the group consisting of substituted or unsubstituted $C_1$-$C_6$ alkyl, halide, —CN, —NO$_2$, —SR$'''$, —OR$'''$, and —NR$'''$R$''$; R$^{11}$ is heteroaryl; each R$^{12}$ is independently selected from the group consisting of substituted or unsubstituted $C_1$-$C_6$ alkyl, halide, —CN, —NO$_2$, —SR$'''$, —OR$'''$, and —NR$'''$R$''$; R$^{13}$ is H or substituted or unsubstituted $C_1$-$C_6$ alkyl; R$^{14}$ is H or substituted or unsubstituted $C_1$-$C_6$ alkyl; each R$'''$ and R$''$ is independently H or substituted or unsubstituted $C_1$-$C_6$ alkyl; X is O or S; p is 0, 1, or 2; q is 0, 1, or 2; and r is 1, 2, 3, 4, or 5.

Para. L. The method of Para. K, wherein R$^9$ is thiazolyl.

Para. M. The method of Para. K or Para. L, wherein R$^{11}$ is 1,2,4-triazolyl.

Para. N. The method of any one of Paras. K-M, wherein X is S.

Para. O. The method of any one of Paras. K-M, wherein X is O.

Para. P. The method of any one of Paras. K-O, wherein p is 0, r is 2, and q is 1.

Para. Q. The method of any one of Paras. A-E, wherein the compound is of Formula IV wherein R$^{15}$ is —C(O)OR$'''$, —C(O)NR$'''$R$''$, —S(O)$_j$R$'''$, —S(O)$_j$NR$'''$R$''$, —NR$''$C(O) R$'''$, —NR$''$C(O)OR$'''$, —NR$''$C(O)NR$'''$R$^p$, —NR$''$S(O)$_j$R$'''$, or —NR$''$S(O)$_j$NR$'''$R$^p$; R$^{16}$ is heteroaryl; each R$^{17}$ is independently selected from the group consisting of substituted or unsubstituted $C_1$-$C_6$ alkyl, halide, —CN, —NO$_2$, —SR$'''$, —OR$'''$, —NR$'''$R$''$, —C(O)R$'''$, —C(O)OR$'''$, —C(O) NR$'''$R$''$, —S(O)$_j$R$'''$, and —S(O)$_j$NR$'''$R$''$; each R$'''$, R$''$, and R$^p$ is independently H or substituted or unsubstituted $C_1$-$C_6$ alkyl; j is 1 or 2; s is 1, 2, or 3; and t is 1, 2, or 3.

Para. R. The method of Para. Q, wherein R$^{16}$ is pyrazolyl.

Para. S. The method of Para. Q or Para. R, wherein R$^{15}$ is —C(O)OR$'''$.

Para. T. The method of any one of Paras. Q-S, wherein s is 1.

Para. U. The method of any one of Paras. Q-S, wherein s is 2.

Para. V. The method of any one of Paras. Q-U, wherein R$^{17}$ is —C(O)OR$'''$.

Para. W. The method of any one of Paras. A-E, wherein the compound is of Formula V wherein R$^{18}$ is substituted or unsubstituted $C_1$-$C_6$ alkyl, —C(O)R$'''$, —C(O)OR$'''$, —C(O) NR$'''$R$''$, —S(O)$_j$R$'''$, or —S(O)$_j$NR$'''$R$''$; R$^{19}$ is H, substituted or unsubstituted $C_1$-$C_6$ alkyl, halide, —CN, —NO$_2$, —SR$'''$, —OR$'''$, —NR$'''$R$''$, or a substituted or unsubstituted heteroaryl ring; each R$'''$ and R$''$ is independently H or substituted or unsubstituted $C_1$-$C_6$ alkyl; Q is —SO$_2$— or —C(O)—; W is S, substituted or unsubstituted $C_1$-$C_6$ alkyl, a substituted or unsubstituted aryl ring, or a substituted or unsubstituted heteroaryl ring; b is 0 or 1; and j is 1 or 2.

Para. X. The method of Para. W, wherein R$^{18}$ is substituted or unsubstituted $C_1$-$C_6$ alkyl or —C(O)R$'''$.

Para. Y. The method of Para. W or Para. X, wherein W is S, $C_1$-$C_6$ alkyl, phenyl, or pyridinyl.

Para. Z. The method of any one of Paras. W-Y, wherein R$^{19}$ is H, $C_1$-$C_6$ alkyl, —NR$'''$R$''$, or 1,2,4-triazolyl optionally substituted with $C_1$-$C_6$ alkyl.

Para. AA. The method of any one of Paras. W-Z, wherein Q is —C(O)—.

Para. AB. The method of any one of Paras. W-Z, wherein Q is —SO$_2$—.

Para. AC. The method of any one of Paras. W-AB, wherein b is 0.

Para. AD. The method of any one of Paras. W-AB, wherein b is 1.

Para. AE. The method of any one of Paras. A-E, wherein the compound of Formula I, Formula II, Formula III, Formula IV, or Formula V, or a stereoisomer, tautomer, or pharmaceutically acceptable salt thereof, is selected from the group consisting of

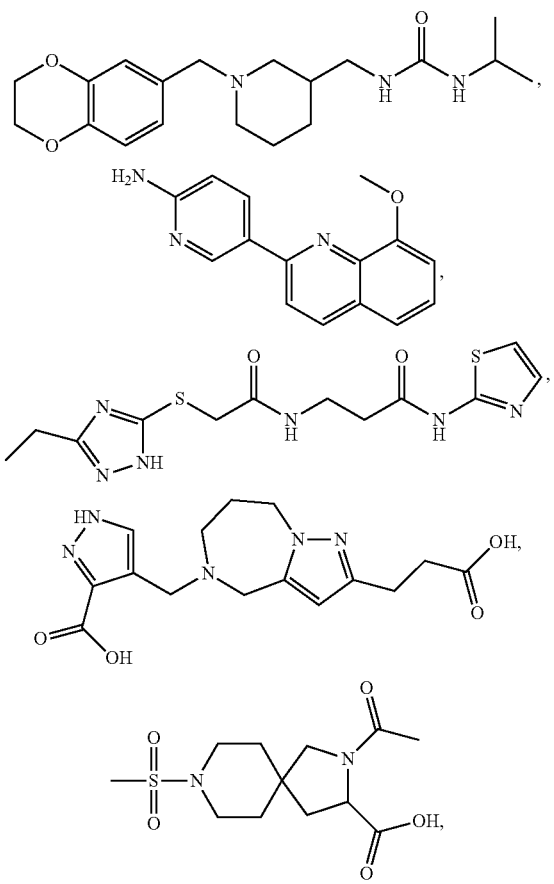

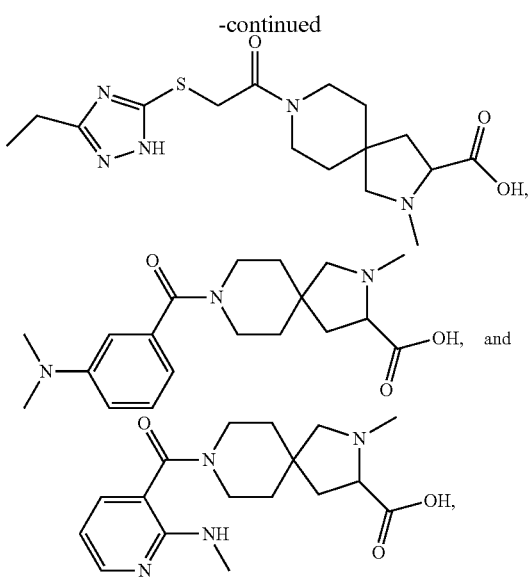

or a stereoisomer, tautomer, or pharmaceutically acceptable salt thereof.

Para. AF. A method to treat cancer or inflammatory disease in a subject in need thereof, the method comprising administering to the subject a therapeutically effective amount of a compound selected from the group consisting of:

1-acetyl-4-{[1-(2-chlorophenyl)-1H-pyrazol-4-yl]methyl}-1,4-diazepan-6-ol;
2-{1-[1-(3-pyridinylmethyl)-4-piperidinyl]-1H-1,2,3-triazol-4-yl}ethanol;
1-(1-{[1-(1,3-thiazol-4-ylcarbonyl)-4-piperidinyl]methyl}-1H-1,2,3-triazol-4-yl)ethanol;
2-acetyl-8-(methylsulfonyl)-2,8-diazaspiro[4.5]decane-3-carboxylic acid;
5-[(4-pyridin-2-ylpiperazin-1-yl)carbonyl]-1H-imidazole-4-carboxylic acid;
8-{[(3-ethyl-1H-1,2,4-triazol-5-yl)thio]acetyl}-2-methyl-2,8-diazaspiro[4.5]decane-3-carboxylic acid;
8-[3-(dimethylamino)benzoyl]-2-methyl-2,8-diazaspiro[4.5]decane-3-carboxylic acid;
2-methyl-8-{[2-(methylamino)-3-pyridinyl]carbonyl}-2,8-diazaspiro[4.5]decane-3-carboxylic acid;
N-[2-(2-amino-1,3-thiazol-4-yl)ethyl]-5-ethyl-2,3-dimethylpyrazolo[1,5-a]pyrimidin-7-amine
N-[(5-acetyl-5,6,7,8-tetrahydro-4H-pyrazolo[1,5-a][1,4]diazepin-2-yl)methyl]-1,3-benzothiazol-2-amine;
N-[(1,5-dimethyl-1H-indazol-3-yl)methyl]-N'-(1-propyl-1H-1,2,3-triazol-4-yl)urea;
N-{[1-(2,3-dihydro-1,4-benzodioxin-6-ylmethyl)piperidin-3-yl]methyl}-N'-isopropylurea;
5-(8-methoxyquinolin-2-yl)pyridin-2-amine; and
3-({[(3-ethyl-1H-1,2,4-triazol-5-yl)thio]acetyl}amino)-N-1,3-thiazol-2-ylpropanamide;
or a stereoisomer, tautomer, or pharmaceutically acceptable salt thereof.

Para. AG. The method of Para. A or Para. AF, wherein the cancer is selected from heart sarcoma, lung cancer, small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; cancer of the gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); cancer of the genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); cancer of the liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); cancer of bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; cancer of the nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiforme, oligodendroglioma, schwannoma, retinoblastoma, congenital tumors), spinal cord neurofibroma, meningioma, glioma, sarcoma); cancer of the reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; cancer of the hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; cancer of the oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; cancer of the skin, for example, malignant melanoma, cutaneous melanoma, basal cell carcinoma, squamous cell carcinoma, Karposi's sarcoma, moles dysplastic nevi, lipoma, angioma, dermatofibroma, and keloids; cancer of the adrenal glands: neuroblastoma; and cancer of other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

Para. AH. A method to stimulate M1 macrophage polarization, the method comprising contacting a macrophage with a compound selected from the group consisting of:
1-acetyl-4-{[1-(2-chlorophenyl)-1H-pyrazol-4-yl]methyl}-1,4-diazepan-6-ol;
2-{1-[1-(3-pyridinylmethyl)-4-piperidinyl]-1H-1,2,3-triazol-4-yl}ethanol;
1-(1-{[1-(1,3-thiazol-4-ylcarbonyl)-4-piperidinyl]methyl}-1H-1,2,3-triazol-4-yl)ethanol;
2-acetyl-8-(methylsulfonyl)-2,8-diazaspiro[4.5]decane-3-carboxylic acid;
5-[(4-pyridin-2-ylpiperazin-1-yl)carbonyl]-1H-imidazole-4-carboxylic acid;
8-{[(3-ethyl-1H-1,2,4-triazol-5-yl)thio]acetyl}-2-methyl-2,8-diazaspiro[4.5]decane-3-carboxylic acid;
8-[3-(dimethylamino)benzoyl]-2-methyl-2,8-diazaspiro[4.5]decane-3-carboxylic acid;
2-methyl-8-{[2-(methylamino)-3-pyridinyl]carbonyl}-2,8-diazaspiro[4.5]decane-3-carboxylic acid;
N-[2-(2-amino-1,3-thiazol-4-yl)ethyl]-5-ethyl-2,3-dimethylpyrazolo[1,5-a]pyrimidin-7-amine
N-[(5-acetyl-5,6,7,8-tetrahydro-4H-pyrazolo[1,5-a][1,4]diazepin-2-yl)methyl]-1,3-benzothiazol-2-amine;
N-[(1,5-dimethyl-1H-indazol-3-yl)methyl]-N'-(1-propyl-1H-1,2,3-triazol-4-yl)urea;
N-{[1-(2,3-dihydro-1,4-benzodioxin-6-ylmethyl)piperidin-3-yl]methyl}-N'-isopropylurea;
5-(8-methoxyquinolin-2-yl)pyridin-2-amine; and
3-({[(3-ethyl-1H-1,2,4-triazol-5-yl)thio]acetyl}amino)-N-1,3-thiazol-2-ylpropanamide;
or a stereoisomer, tautomer, or pharmaceutically acceptable salt thereof.

Para. AI. A method to inhibit M2 macrophage polarization, the method comprising contacting a macrophage with a compound selected from the group consisting of:
1-acetyl-4-{[1-(2-chlorophenyl)-1H-pyrazol-4-yl]methyl}-1,4-diazepan-6-ol;
2-{1-[1-(3-pyridinylmethyl)-4-piperidinyl]-1H-1,2,3-triazol-4-yl}ethanol;
1-(1-{[1-(1,3-thiazol-4-ylcarbonyl)-4-piperidinyl]methyl}-1H-1,2,3-triazol-4-yl)ethanol;
2-acetyl-8-(methylsulfonyl)-2,8-diazaspiro[4.5]decane-3-carboxylic acid;
5-[(4-pyridin-2-ylpiperazin-1-yl)carbonyl]-1H-imidazole-4-carboxylic acid;
8-{[(3-ethyl-1H-1,2,4-triazol-5-yl)thio]acetyl}-2-methyl-2,8-diazaspiro[4.5]decane-3-carboxylic acid;
8-[3-(dimethylamino)benzoyl]-2-methyl-2,8-diazaspiro[4.5]decane-3-carboxylic acid;
2-methyl-8-{[2-(methylamino)-3-pyridinyl]carbonyl}-2,8-diazaspiro[4.5]decane-3-carboxylic acid;
N-[2-(2-amino-1,3-thiazol-4-yl)ethyl]-5-ethyl-2,3-dimethylpyrazolo[1,5-a]pyrimidin-7-amine
N-[(5-acetyl-5,6,7,8-tetrahydro-4H-pyrazolo[1,5-a][1,4]diazepin-2-yl)methyl]-1,3-benzothiazol-2-amine;
N-[(1,5-dimethyl-1H-indazol-3-yl)methyl]-N'-(1-propyl-1H-1,2,3-triazol-4-yl)urea;
N-{[1-(2,3-dihydro-1,4-benzodioxin-6-ylmethyl)piperidin-3-yl]methyl}-N'-isopropylurea;
5-(8-methoxyquinolin-2-yl)pyridin-2-amine; and
3-({[(3-ethyl-1H-1,2,4-triazol-5-yl)thio]acetyl}amino)-N-1,3-thiazol-2-ylpropanamide;
or a stereoisomer, tautomer, or pharmaceutically acceptable salt thereof.

Para. AJ. The method of Para. AH or Para. A, wherein the contacting of the macrophage is performed in an in vitro assay.

Para. AK. The method of Para. AH or Para. A, wherein the contacting of the macrophage is performed in an in vivo assay.

Para. AL. The method of Para. AH or Para. A, wherein the method is performed in vitro.

Para. AM. The method of Para. AH or Para. A, wherein the method is performed in vivo.

Para. AN. The method of Para. A or Para. AF, wherein the subject is a mammal.

Para. AO. The method of Para. A or Para. AF, wherein the subject is a human.

Para. AP. The method of Para. A or Para. AF, wherein the compound is administered locally.

Para. AQ. The method of Para. A or Para. AF, wherein the compound is administered systemically.

Para. AR. The method of Para. A or Para. AF, wherein the cancer or inflammatory disease is selected from the group consisting of acute respiratory distress syndrome, coronavirus and other viral infections, sepsis associated with MRSA and other bacterial infections, COPD, NASH, cirrhosis, Crohn's disease, multiple sclerosis, lung cancer, breast cancer, pancreatic cancer, liver cancer, glioblastoma, and melanoma.

Other embodiments are set forth in the following claims.

What is claimed is:

1. A method to treat cancer or inflammatory disease in a subject in need thereof, the method comprising administering to the subject a compound selected from the group consisting of:
   1-acetyl-4-{[1-(2-chlorophenyl)-1H-pyrazol-4-yl]methyl}-1,4-diazepan-6-ol;
   2-{1-[1-(3-pyridinylmethyl)-4-piperidinyl]-1H-1,2,3-triazol-4-yl}ethanol;
   1-(1-{[1-(1,3-thiazol-4-ylcarbonyl)-4-piperidinyl]methyl}-1H-1,2,3-triazol-4-yl)ethanol;
   2-acetyl-8-(methylsulfonyl)-2,8-diazaspiro[4.5]decane-3-carboxylic acid;
   5-[(4-pyridin-2-ylpiperazin-1-yl)carbonyl]-1H-imidazole-4-carboxylic acid;
   8-{[(3-ethyl-1H-1,2,4-triazol-5-yl)thio]acetyl}-2-methyl-2,8-diazaspiro[4.5]decane-3-carboxylic acid;
   8-[3-(dimethylamino)benzoyl]-2-methyl-2,8-diazaspiro[4.5]decane-3-carboxylic acid;
   2-methyl-8-{[2-(methylamino)-3-pyridinyl]carbonyl}-2,8-diazaspiro[4.5]decane-3-carboxylic acid;
   N-[2-(2-amino-1,3-thiazol-4-yl)ethyl]-5-ethyl-2,3-dimethylpyrazolo[1,5-a]pyrimidin-7-amine;
   N-[(5-acetyl-5,6,7,8-tetrahydro-4H-pyrazolo[1,5-a][1,4]diazepin-2-yl)methyl]-1,3-benzothiazol-2-amine;
   N-[(1,5-dimethyl-1H-indazol-3-yl)methyl]-N'-(1-propyl-1H-1,2,3-triazol-4-yl)urea;
   4-((2-(2-carboxyethyl)-7,8-dihydro-4H-pyrazolo[1,5-a][1,4]diazepin-5(6H)-yl)methyl)-1H-pyrazole-3-carboxylic acid;
   N-{[1-(2,3-dihydro-1,4-benzodioxin-6-ylmethyl)piperidin-3-yl]methyl}-N'-isopropylurea;
   5-(8-methoxyquinolin-2-yl)pyridin-2-amine; and
   3-({[(3-ethyl-1H-1,2,4-triazol-5-yl)thio]acetyl}amino)-N-1,3-thiazol-2-ylpropanamide;

or a stereoisomer, tautomer, or pharmaceutically acceptable salt thereof;
wherein the cancer is selected from lymphoma, leukemia, lung cancer, breast cancer, pancreatic cancer, liver cancer, glioblastoma, and melanoma.

2. A method to stimulate M1 macrophage polarization, the method comprising contacting a macrophage with a compound selected from the group consisting of:
- 1-acetyl-4-{[1-(2-chlorophenyl)-1H-pyrazol-4-yl]methyl}-1,4-diazepan-6-ol;
- 2-{1-[1-(3-pyridinylmethyl)-4-piperidinyl]-1H-1,2,3-triazol-4-yl}ethanol;
- 1-(1-{[1-(1,3-thiazol-4-ylcarbonyl)-4-piperidinyl]methyl}-1H-1,2,3-triazol-4-yl)ethanol;
- 2-acetyl-8-(methylsulfonyl)-2,8-diazaspiro[4.5]decane-3-carboxylic acid;
- 5-[(4-pyridin-2-ylpiperazin-1-yl)carbonyl]-1H-imidazole-4-carboxylic acid;
- 8-{[(3-ethyl-1H-1,2,4-triazol-5-yl)thio]acetyl}-2-methyl-2,8-diazaspiro[4.5]decane-3-carboxylic acid;
- 8[3-(dimethylamino)benzoyl]-2-methyl-2,8-diazaspiro[4.5]decane-3-carboxylic acid;
- 2-methyl-8-{[2-(methylamino)-3-pyridinyl]carbonyl}-2,8-diazaspiro[4.5]decane-3-carboxylic acid;
- N-[2-(2-amino-1,3-thiazol-4-yl)ethyl]-5-ethyl-2,3-dimethylpyrazolo[1,5-a]pyrimidin-7-amine;
- N-[(5-acetyl-5,6,7,8-tetrahydro-4H-pyrazolo[1,5-a][1,4]diazepin-2-yl)methyl]-1,3-benzothiazol-2-amine;
- N-[(1, 5-dimethyl-1H-indazol-3-yl)methyl]-N'-(1-propyl-1H-1,2,3-triazol-4-yl)urea;
- 4-((2-(2-carboxyethyl)-7,8-dihydro-4H-pyrazolo[1,5-a][1,4]diazepin-5(6H)-yl)methyl)-1H-pyrazole-3-carboxylic acid;
- N-{[1-(2,3-dihydro-1,4-benzodioxin-6-ylmethyl)piperidin-3-yl]methyl}-N'-isopropylurea;
- 5-(8-methoxyquinolin-2-yl)pyridin-2-amine; and
- 3-({[(3-ethyl-1H-1,2,4-triazol-5-yl)thio]acetyl}amino)-N-1,3-thiazol-2-ylpropanamide;

or a stereoisomer, tautomer, or pharmaceutically acceptable salt thereof.

3. A method to inhibit M2 macrophage polarization, the method comprising contacting a macrophage with a compound selected from the group consisting of:
- 1-acetyl-4-{[1-(2-chlorophenyl)-1H-pyrazol-4-yl]methyl}-1,4-diazepan-6-ol;
- 2-{1-[1-(3-pyridinylmethyl)-4-piperidinyl]-1H-1,2,3-triazol-4-yl}ethanol;
- 1-(1-{[1-(1,3-thiazol-4-ylcarbonyl)-4-piperidinyl]methyl}-1H-1,2,3-triazol-4-yl)ethanol;
- 2-acetyl-8-(methylsulfonyl)-2,8-diazaspiro[4.5]decane-3-carboxylic acid;
- 5-[(4-pyridin-2-ylpiperazin-1-yl)carbonyl]-1H-imidazole-4-carboxylic acid;
- 8-{[(3-ethyl-1H-1,2,4-triazol-5-yl)thio]acetyl}-2-methyl-2,8-diazaspiro[4.5]decane-3-carboxylic acid;
- 8-[3-(dimethylamino)benzoyl]-2-methyl-2,8-diazaspiro[4.5]decane-3-carboxylic acid;
- 2-methyl-8-{[2-(methylamino)-3-pyridinyl]carbonyl}-2,8-diazaspiro[4.5]decane-3-carboxylic acid;
- N-[2-(2-amino-1,3-thiazol-4-yl)ethyl]-5-ethyl-2,3-dimethylpyrazolo[1,5-a]pyrimidin-7-amine;
- N-[(5-acetyl-5,6,7,8-tetrahydro-4H-pyrazolo[1,5-a][1,4]diazepin-2-yl)methyl]-1,3-benzothiazol-2-amine;
- N-[(1,5-dimethyl-1H-indazol-3-yl)methyl]-N'-(1-propyl-1H-1,2,3-triazol-4-yl)urea;
- 4-((2-(2-carboxyethyl)-7,8-dihydro-4H-pyrazolo[1,5-a][1,4]diazepin-5(6H)-yl)methyl)-1H-pyrazole-3-carboxylic acid;
- N-{[1-(2,3-dihydro-1,4-benzodioxin-6-ylmethyl)piperidin-3-yl]methyl}-N'-isopropylurea;
- 5-(8-methoxyquinolin-2-yl)pyridin-2-amine; and
- 3-({[(3-ethyl-1H-1,2,4-triazol-5-yl)thio]acetyl}amino)-N-1,3-thiazol-2-ylpropanamide;

or a stereoisomer, tautomer, or pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,344,559 B2 | Page 1 of 1 |
| APPLICATION NO. | : 16/911894 | |
| DATED | : May 31, 2022 | |
| INVENTOR(S) | : Judith Varner et al. | |

It is certified that error appears in the above-identified patent and that said Letters Patent is hereby corrected as shown below:

In the Specification

Column 1, Line 11, after "under" insert --DE027325,--

Column 1, Line 12, after "CA167426" insert --, and CA226909--

Colum 1, Line 13, delete "(NIH)"

Signed and Sealed this
Twelfth Day of September, 2023

Katherine Kelly Vidal
*Director of the United States Patent and Trademark Office*